(12) United States Patent
Maiefski et al.

(10) Patent No.: US 7,083,395 B2
(45) Date of Patent: Aug. 1, 2006

(54) PUMP SYSTEM FOR PUMPING LIQUEFIED GASES

(76) Inventors: Romaine Maiefski, 1312 Hollins Rd., Oceanside, CA (US) 92056; Jon Guy, 3578 Avenida Pantera, Carlsbad, CA (US) 92002

( * ) Notice: Subject to any disclaimer, the term of this patent is extended or adjusted under 35 U.S.C. 154(b) by 16 days.

(21) Appl. No.: 10/146,784

(22) Filed: May 15, 2002

(65) Prior Publication Data

US 2003/0215341 A1    Nov. 20, 2003

(51) Int. Cl.
*F04B 39/06* (2006.01)

(52) U.S. Cl. .................. 417/228; 417/454; 417/373; 417/312; 417/571; 92/72; 92/129; 74/55; 74/56

(58) Field of Classification Search ........... 417/228, 417/454, 373, 312, 571, 313; 92/72, 129; 74/55, 56

See application file for complete search history.

(56) References Cited

U.S. PATENT DOCUMENTS

| | | | | |
|---|---|---|---|---|
| 3,744,935 A | * | 7/1973 | Magni ................. 417/370 |
| 4,600,365 A | * | 7/1986 | Riggenmann ............ 417/246 |
| 4,724,087 A | * | 2/1988 | Perrut .................. 210/788 |
| 4,998,433 A | * | 3/1991 | Stumpf et al. ........... 73/25.01 |
| 5,147,538 A | * | 9/1992 | Wright et al. ........... 210/198.2 |
| 5,180,293 A | * | 1/1993 | Hartl ................... 417/366 |
| 5,511,955 A | * | 4/1996 | Brown et al. ........... 417/259 |
| 5,738,498 A | * | 4/1998 | Allington et al. ......... 417/53 |
| 5,750,027 A | * | 5/1998 | Allington et al. ........ 210/511 |
| 6,394,762 B1 | * | 5/2002 | Collingborn et al. ..... 417/254 |

* cited by examiner

*Primary Examiner*—Timothy S. Thorpe
*Assistant Examiner*—Emmanuel Sayoc
(74) *Attorney, Agent, or Firm*—Perkins Coie, LLP

(57) ABSTRACT

Under one aspect of the present invention, a liquefied gas pump assembly is coupleable to a source of liquefied gas. A cooling assembly is positioned generally adjacent to a pump module. The cooling assembly has a converging pump-head-receiving aperture, a fluid inlet line and a fluid outlet line in fluid communication with the source of liquefied gas and in fluid communication with the pump-head-receiving aperture. A pump head assembly is removably retained in the pump-head-receiving aperture so that a portion of the cooling assembly is between the pump head assembly and the pump module. The pump head assembly has a converging shape and being sized to engage the cooling assembly in a wedged configuration when the pump assembly is in an installed position in the cooling assembly. The pump head assembly has a fluid inlet pathway abutting in sealable engagement with the fluid inlet line of the cooling assembly. The pump head assembly also has a fluid outlet pathway abutting in sealable engagement with the fluid outlet line the cooling assembly, the pump head assembly being operably coupled to the pump driver of the pump module to provide a flow of the liquefied gas from the fluid inlet line, through the pump head assembly, and to the outlet line.

38 Claims, 16 Drawing Sheets

PUMP SYSTEM FOR PUMPING LIQUEFIED GASES

TECHNICAL FIELD

The present invention is directed to apparatus and methods for pumping liquefied gases, and more particularly, to apparatus and methods for providing a chilled pump head assembly for pumping the liquefied gases while maintaining easy accessibility and serviceability for the pump head assembly.

BACKGROUND

Supercritical fluid chromatography (SFC) and supercritical fluid extraction typically use highly compressible fluids, such as liquefied carbon dioxide ($CO_2$) or other liquefied gases, as a carrier fluid within the systems. An example of a system utilizing the liquid $CO_2$ flow in a fluid system is the high throughput purification system discussed in U.S. Pat. No. 6,309,541, which is incorporated herein by reference thereto. These liquefied gases are highly compressible, so they must be kept at low temperatures and high pressure when pumped to prevent cavitation in the fluid system. Systems utilizing liquid $CO_2$ typically must maintain the liquid $CO_2$ at approximately 0° C. or lower throughout the pumping process.

Pump assemblies have been developed that cool the pump head to help maintain the liquid $CO_2$ in its chilled condition during the pumping process. Such pump assemblies typically utilize a variety of heat exchangers or thermoelectric cooling systems that mount on the outside of the pump assembly and cover the pump head. Other systems have utilized a recirculating cooling bath system that pumps chilled fluid through or around the pump head to chill the pump head. These pump designs, however, provide a significant amount of hardware and components that severely limit easy access to and serviceability of the pump head. As a result, maintenance of the pump head can require significant down time for the system during the routine maintenance or repair of the pump head or its components.

The process of pumping the liquid $CO_2$ or other liquefied gas results in exposing the components of the pump assembly to very cold and harsh conditions. These conditions can significantly impact the accuracy or operational life of a pump assembly. Liquid $CO_2$ pump assemblies encounter a further difficulty due to contaminants within the liquefied gas being pumped. These contaminants, when pumped through the pump head, can wear excessively on the pump head's valves and seals. In some situations, valves in pump heads must be serviced after only a short length of actual service time. Pump seals also often require servicing as a result of wear caused by contaminants in the liquefied gas. The conventional chilled pump assemblies that have limited access to the pump heads because of the chilling components are difficult to service quickly. As a result, the pump assemblies are often taken off-line for a significant period of time to perform the servicing or routine maintenance, thereby decreasing the actual operational time of the fluid system.

SUMMARY

Under one aspect of the present invention, a liquefied gas pump assembly is provided that has a pump module with pump driver. A cooling assembly is positioned generally adjacent to the pump module. The cooling assembly has a fluid inlet line and a fluid outlet line in fluid communication with a converging pump-head-receiving aperture. The fluid intake line is in communication with a source of liquefied gas. A pump head assembly is removably retained in the pump-head-receiving aperture so that a portion of the cooling assembly is between the pump head assembly and the pump module. The pump head assembly has a converging shape sized to engage the cooling assembly in a wedged configuration when the pump assembly is in an installed position in the cooling assembly. The pump head assembly has a fluid inlet pathway abutting in sealable engagement with the fluid inlet line of the cooling assembly. The pump head assembly also has a fluid outlet pathway abutting in sealable engagement with the fluid outlet line of the cooling assembly. The pump head assembly is operably coupled to the pump driver of the pump module.

Another embodiment of the invention provides a pump assembly having a pump module and a cooling assembly connected to the pump module. The cooling assembly has a pump-head-receiving aperture positioned to be directly accessible when the cooling assembly is connected to the pump module. The cooling assembly has a fluid inlet line and an outlet line in fluid communication with the pump-head-receiving aperture. A pump head assembly is removably retained in the pump-head-receiving aperture with a portion of the cooling assembly being between the pump head assembly and the pump module. The pump head assembly has a fluid inlet pathway in fluid communication with the fluid inlet line and a fluid outlet pathway in fluid communication with the fluid outlet line. The pump head assembly is accessible and removable from the cooling assembly while the cooling assembly is adjacent to the pump module. The pump head assembly has a fluid inlet pathway in fluid communication with the fluid inlet line and a fluid outlet pathway in fluid communication with the fluid outlet line.

In another embodiment of the invention, a pump assembly has a pump module, a cooling assembly, and a pump head assembly. The cooling assembly is connected to the pump module and has a pump-head-receiving aperture positioned to be directly accessible when the cooling assembly is connected to the pump module. The pump head assembly is removably retained in the pump-head-receiving aperture with the cooling assembly being between the pump head assembly and the pump module.

In another embodiment of the invention, a pump system has a cooling assembly with a pump-head-receiving aperture and a pump head assembly removably retained in the pump-head-receiving aperture. A pump driver is coupled to the pump head assembly. The pump driver engages the pump head assembly for reciprocal movement of a portion of the pump head assembly along an aspiration stroke and a discharge stroke. The discharge portion includes a fluid compression portion and a fluid delivery portion. The fluid compression stroke is approximately 30 percent of the full discharge stroke, and the fluid delivery portion is approximately 70 percent of the full discharge stroke. The pump driver includes a rotating cam that engages the drive shaft. The cam is shaped to permit the full aspiration stroke upon rotation of the cam through approximately 130°–150°. The cam causes the compression portion of the discharge stroke upon rotation through approximately 30°–50°. The cam also causes the fluid delivery portion of the discharge stroke upon rotation through approximately 170°–190°.

Yet another embodiment provides a fluid flow system through which liquefied gas is carried. The system is connectable to a liquefied gas source and a lubricating/solvating liquid source. The system has a fluid line coupleable to the liquefied gas source and configured to carry a flow of liquefied gas therethrough. A lubricating/solvating liquid injector is connected to the fluid line. An injector pump is coupled to the lubricating/solvating liquid injector and coupleable to the lubricating/solvating liquid source. The injector pump is positioned to pump the lubricating/solvating liquid into the flow of liquefied gas to provide a mixture of liquefied gas and solvating liquid. A liquefied-gas pump assembly is connected to the fluid line downstream of the lubricating/solvating liquid injector. The pump assembly is positioned to receive the flow of the mixture. The liquefied gas pump assembly has a plurality of check valves and pump seals in fluid communication with the flow of the mixture and being at least partially lubricated by the mixture as the mixture flows past the liquefied gas pump assembly.

DETAILED DESCRIPTION

In the following description, certain specific details are set forth in order to provide a thorough understanding of various embodiments of the invention. One skilled in the art will understand, however, that the invention may be practiced without some of these details. In other instances, well known structures associated with liquefied-gas pumping systems and related apparatus have not been shown or described in detail to avoid unnecessarily obscuring the description of the embodiments of the invention.

Figure 1:
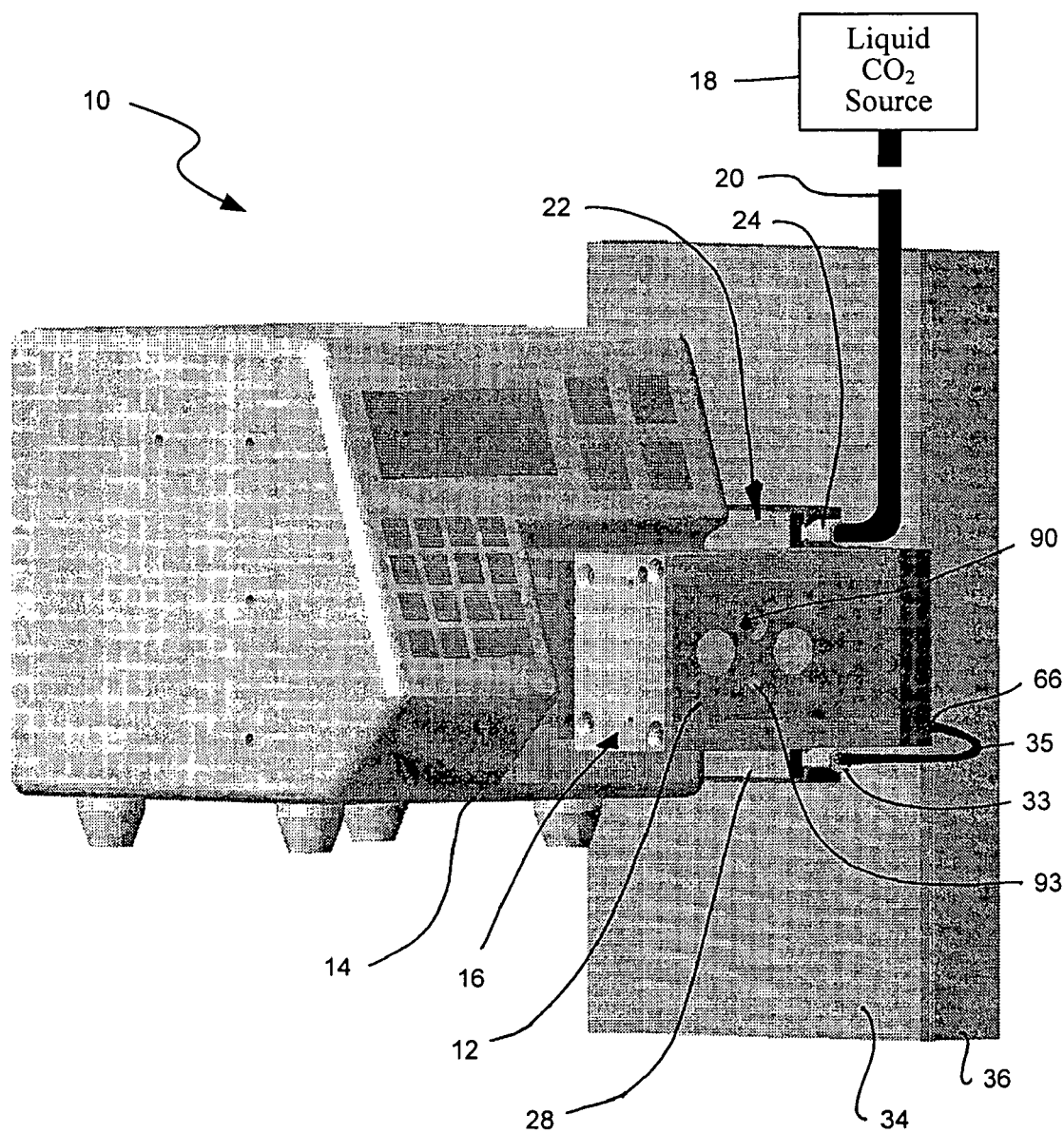
FIG. 1 is a front isometric view of a pump system usable for pumping liquid $CO_2$, the system having a pump module, a pump head assembly, a cooling jacket, and a heat exchanger system in accordance with one embodiment of the present invention.

FIG. 1 is a front isometric view of a liquefied-gas pump system 10 in accordance with one embodiment of the present invention. The pump system 10 of the illustrated embodiment is part of a supercritical fluid chromatography (SFC) system that utilizes liquid $CO_2$ as the carrier fluid throughout the fluid lines in the system. The pump system 10 is also usable in systems for supercritical fluid extraction or other similar systems that use liquefied gases.

The pump system 10 of the illustrated embodiment includes a pump head assembly 12 surrounded by a cooling jacket 16 and connected to a pump module 14. In the illustrated embodiment, the pump module 14 is a PU-1580 Intelligent HPLC Pump manufactured by Jasco Corporation of Tokyo, Japan. Other pump modules, such as Series 1500 Dual Head Digital HPLC Pump manufactured by Scientific Systems of State College, Pennsylvania, can be used. The cooling jacket 16 is positioned adjacent to the pump system 10 and is made of a thermally conductive material, such as nickel-plated copper or aluminum. As discussed in greater detail below, the cooling jacket 16 is adapted to chill the pump head assembly 12 to approximately 0° C. or another selected low temperature as required by the liquefied gas in the fluid system.

Figure 2:
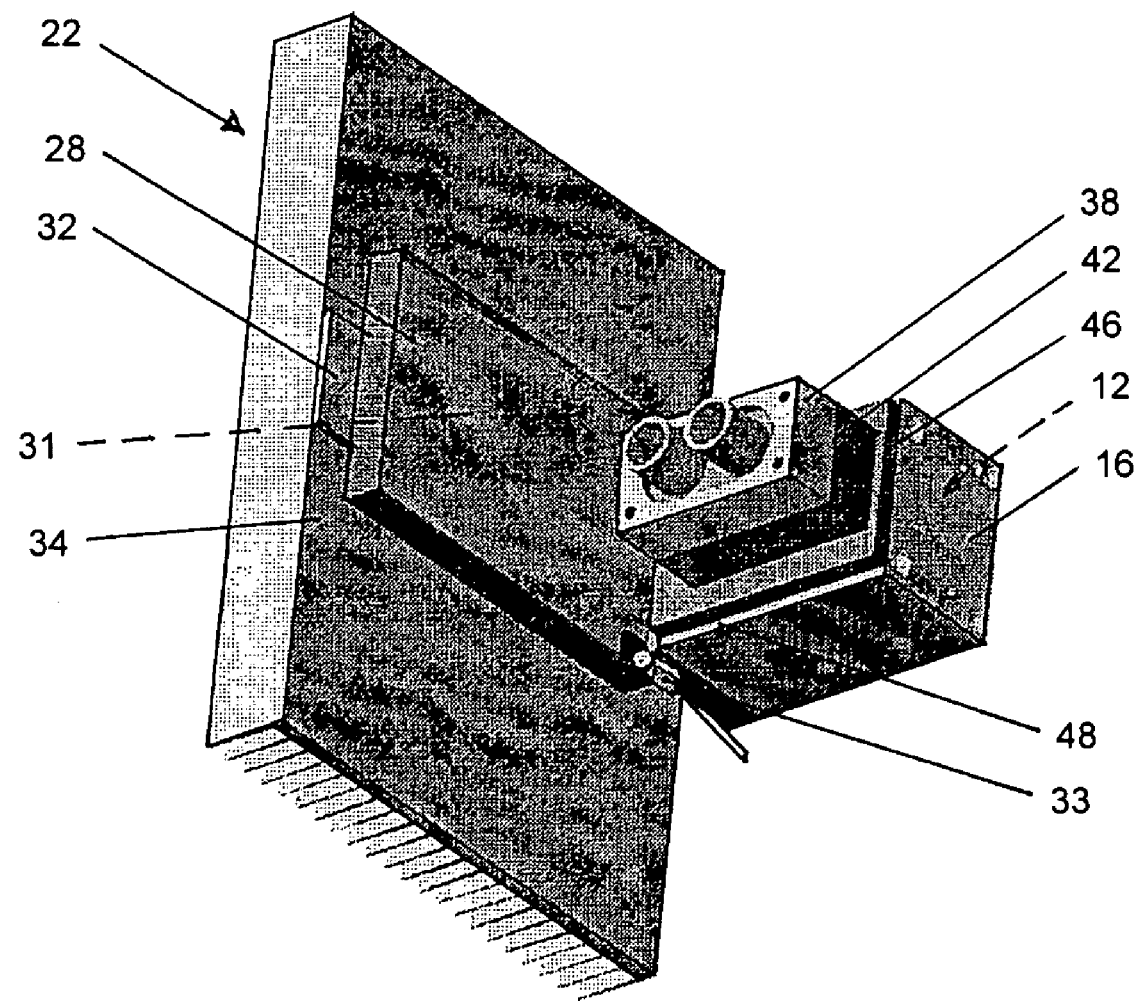
FIG. 2 is a rear isometric view of the pump head assembly, cooling jacket, and heat exchanger assembly shown removed from the pump module of FIG. 1.
Figure 3:
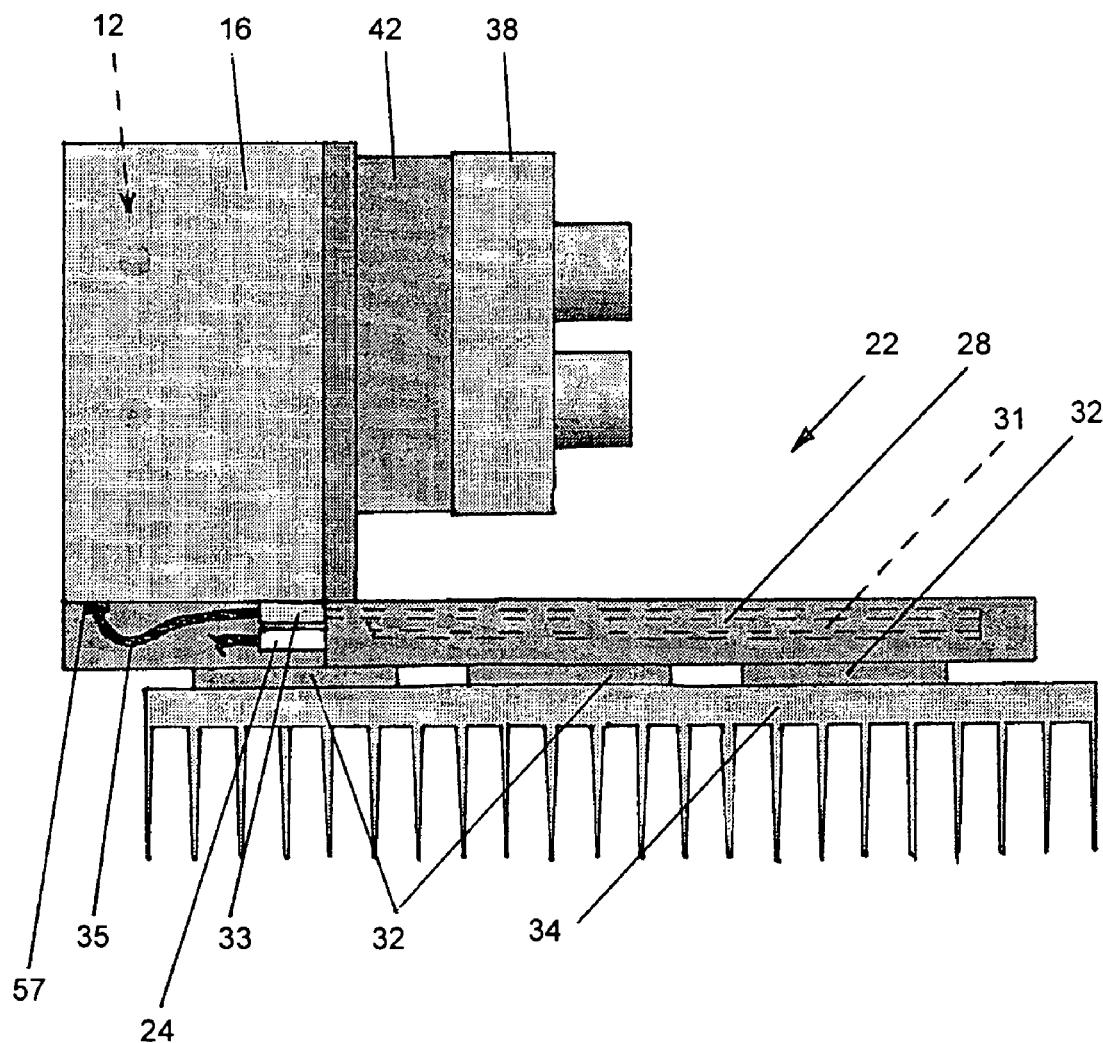
FIG. 3 is a top plan view of the pump head assembly, cooling jacket, insulator and heat exchanger assembly shown removed from the pump module of FIG. 1.

The pump system 10 is coupled to a source 18 of liquid $CO_2$ via small-bore fluid lines 20 (shown schematically). The fluid lines 20 carry the liquid $CO_2$ to a chiller assembly 22 to chill the liquid $CO_2$ before it flows into the pump head assembly 12. FIG. 2 is a rear isometric view of the pump head assembly 12, the cooling jacket, and the chiller assembly 22 shown removed from the pump module 14 of FIG. 1. FIG. 3 is an enlarged top plan view of the pump head assembly 12, the cooling jacket, and the chiller assembly 22 shown removed from the pump module of FIG. 1. The chiller assembly 22 includes a thermal transfer plate 28 mounted directly to the side of the cooling jacket 16 and alongside the pump head assembly 12. Accordingly, the chiller assembly 22 does not interfere with access to the pump head assembly 12 from the front of the pump system 10. The thermal transfer plate 28 in this embodiment also acts as a heat sink attached to the cooling jacket 16 and the pump head assembly 12 to assist in chilling these elements.

The chilled liquid $CO_2$ enters the chiller assembly 22 through an inlet fitting 24 (FIG. 3) on the thermal transfer plate 28. The thermal transfer plate 28 contains a small-bore fluid line 29 connected to the inlet fitting 24, and the fluid line forms a chilling coil 31 through which the liquid $CO_2$ flows. A plurality of peltier thermoelectric coolers 32 (FIG. 3) is mounted to the outside of the thermal transfer plate 28 and adjacent to the chilling coil 31. The thermoelectric coolers 32 are mounted so the cold side of each cooler is positioned against the thermal transfer plate 28. These thermoelectric coolers 32 are designed to thermoelectrically draw heat out of the liquid $CO_2$ via the thermal transfer plate 28 as it flows through the chilling coil 31. The thermoelectric coolers 32 are sandwiched between the thermal transfer plate 28 and a heat sink 34 so that the warm sides of the coolers are against the heat sink.

The heat sink 34 dissipates the heat drawn from the thermal transfer plate 28 and the chilling coil 31. The heat sink 34 has a plurality of elongated fins that dissipate the heat through natural convection. The chilled liquid $CO_2$ flows out of the chilling coil 31 and out of the thermal transfer plate 28 through an outlet fitting 33 (FIG. 2) on the thermal transfer plate. The chilled liquid $CO_2$ flows from the chiller assembly's outlet fitting 33, through a small-bore line 35, and into a fluid inlet port 57 in the cooling jacket 16 that surrounds the pump head assembly 12.

The chiller assembly 22 and the heat sink 34 are mounted close to the pump head assembly 12 and the cooling jacket 16 but in locations that do not obstruct direct access to the pump head assembly from the front of the pump system 10. This substantially unobstructed position of the pump head assembly 12 provides for easy accessibility when the pump head assembly requires service or routine maintenance. The chiller assembly 22, however, is close enough to the pump head assembly 12 and the cooling jacket 16 so the chilled liquid $CO_2$ does not travel far before being drawn into the pump head assembly.

Figure 4:
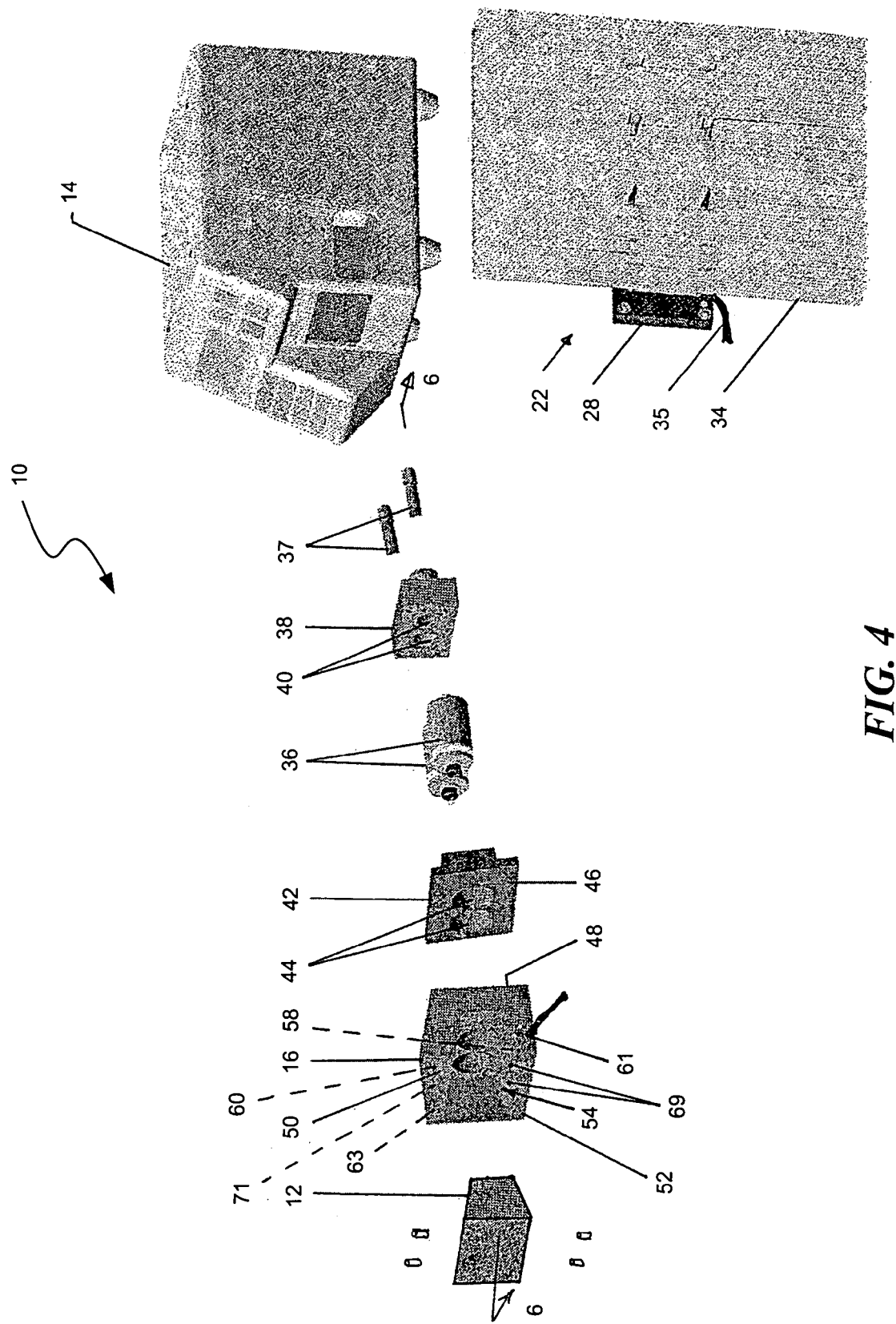
FIG. 4 is a partially exploded isometric view of the pump module, pump head assembly, cooling jacket, and heat exchanger assembly of FIG. 1.

FIG. 4 is a partially exploded isometric view of the pump system 10, showing the cooling jacket 16, the pump head assembly 12, and other components of the system. The pump system 10 in the illustrated embodiment provides a dual pump configuration with a pair of side-by-side reciprocating piston assemblies 36 connected to the pump head assembly 12. The piston assemblies 36 are operatively coupled together and alternately activated by the same stepper motor so as to provide a substantially continuous flow of liquid $CO_2$ through the pump head assembly 12 and along the liquid system. The piston assemblies 36 are configured so as to minimize pulsing of the liquid $CO_2$ as it is pumped along the liquid system. In one embodiment, an additional pulse damper can be used downstream of the pump head assembly 12 and cooling jacket 16 to further extinguish or prevent pulsing that may occur in the flow of liquid $CO_2$.

As best seen in FIGS. 2 and 4, the pump head assembly 12 is contained in the cooling jacket 16, and the cooling jacket is attached to an insulator block 42. The insulator block 42 is sandwiched between the cooling jacket 16 and a mounting block 38. The mounting block 38 is securely retained in the pump module 14 adjacent to a pair of pump drivers 37. The insulator block 42 has a pair of open internal cylinders 44 coaxially aligned with a pair of open cylinders 40 in the mounting block 38. Each of the piston assemblies 36 is positioned in a respective pair of the open cylinders 44 and 40 and aligned with one of the pump drivers 37. In the illustrated embodiment, the insulator block 42 is made of an insulative epoxy-bonded fiberglass material that thermally insulates the piston assemblies 36 from the cooling jacket 16 and the pump head assembly 12. This insulator block 42 effectively minimizes the thermal pathways between the pump drivers 37 and the chilled pump head assembly 12. In the illustrated embodiment, the mounting block 38 is securely fastened with conventional fasteners to the front side of the pump module 14 so that the open cylinders 40 extend into blind receptacles in the pump module adjacent to the pump drivers 37. Accordingly, the piston assemblies 36 are securely held in place for activation by the pump drivers 37 when the pump head assembly 12 is installed on the pump module 14.

The cooling jacket 16 has a rear wall 48 that abuts the insulator block's front face 46. The cooling jacket 16 also has a pair of cylindrical apertures therethrough coaxially aligned with the insulator block's open internal cylinders 44. The cooling jacket 16 and the insulator block 42 are securely retained in position adjacent to the pump module 14. In the illustrated embodiment, the cooling jacket 16 is made from a copper alloy containing deoxidized tellurium, namely CuTeP, commercially known as C14500. This copper alloy is plated with electroless nickel so as to uniformly plate the cooling jacket 16 with an acceptably chemically resistant material suitable for use with the liquid $CO_2$ and other solvents in the fluid system. In another embodiment, the cooling jacket 16 can be made primarily out of aluminum or other sufficiently thermally conductive material.

Figure 5:
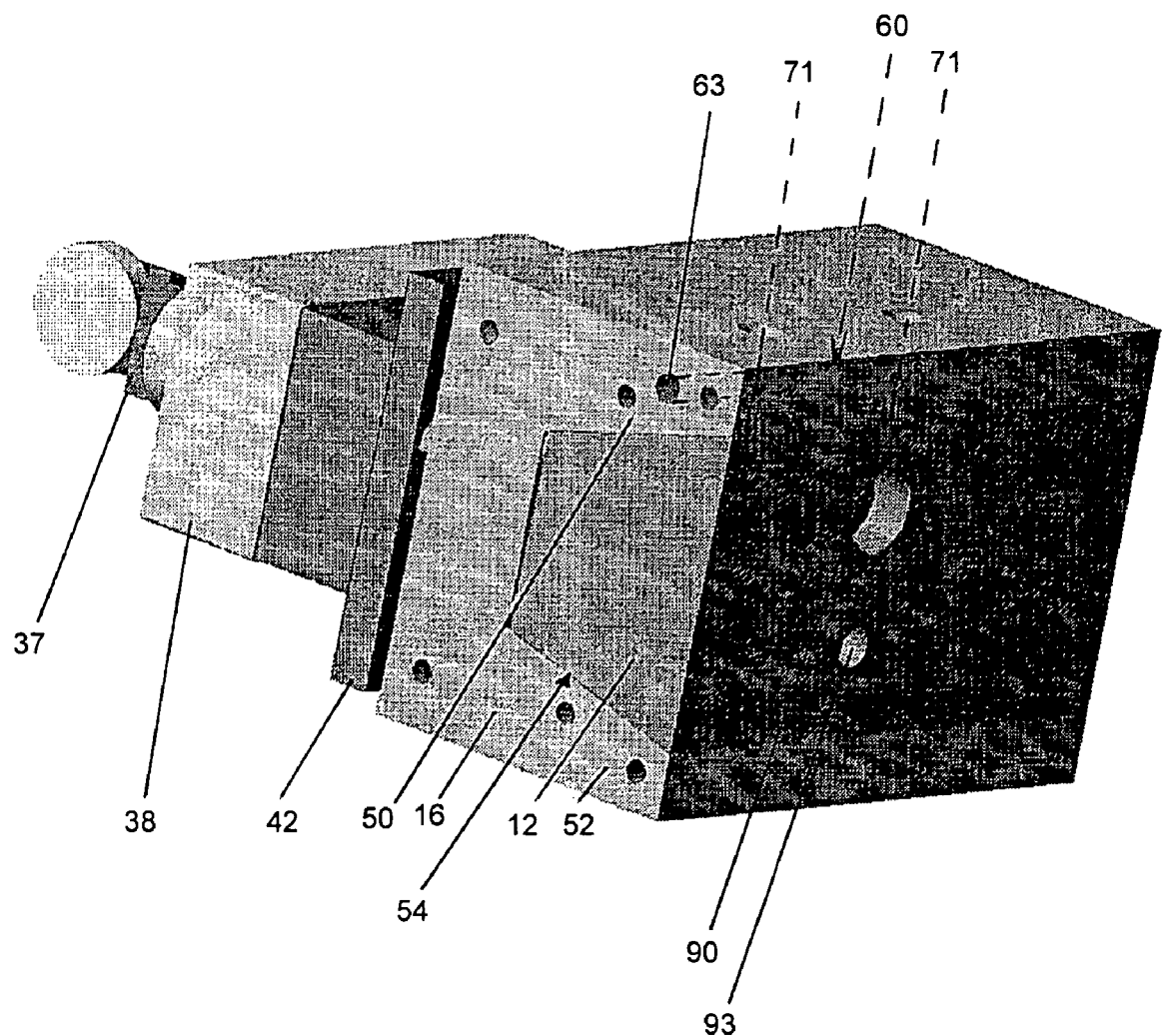
FIG. 5 is an enlarged isometric view of the pump head module and cooling jacket shown removed from the pump module and heat exchanger of FIG. 1.

FIG. 5 is an enlarged isometric view of the cooling jacket 16 surrounding the pump head assembly 12 and being mounted to the insulator block 42 and the mounting block 38. Referring now to FIGS. 4 and 5, the cooling jacket 16 has a lower wall portion 52 spaced apart from an upper wall portion 50 to define a pump head receiving aperture 54 therebetween. The pump head receiving aperture 54 removably receives the pump head assembly 12. The lower wall portion 52 in the illustrated embodiment includes a bore extending inwardly from one side of the lower wall portion to define a fluid inlet channel 61. The fluid inlet channel 61 receives the chilled $CO_2$ from the chiller assembly 22 via the small-bore line 35 extending from the chiller assembly 22 (FIG. 3).

The fluid inlet channel 61 is connected to two flow outlets 69 formed by bores in the lower wall portion 52 of the cooling jacket 16. The two flow outlets 69 extend from the fluid inlet channel 61 to the pump head receiving aperture 54, thereby defining an integral lower flow manifold 58 in the cooling jacket 16. Each of the two flow outlets 69 sealably connect to the pump head assembly 12 when the pump head assembly is installed in the cooling jacket 16. Similar to the cooling jacket's lower wall portion 52, the upper wall portion has an integral upper flow manifold 60 that carries the flow of liquid $CO_2$ through a portion of cooling jacket 16. The upper flow manifold 60 is formed by a pair of flow inlets 71 that each extend from the pump head receiving aperture 54 and connect to a single flow outlet channel 63 formed by a bore in the upper wall portion 50. Accordingly, the upper flow manifold 60 receives two alternating flows of pumped liquid $CO_2$ from the pump head assembly 12 and direct the flows through the fluid outlet channel 63 to the edge of the upper wall portion 50.

Figure 6:
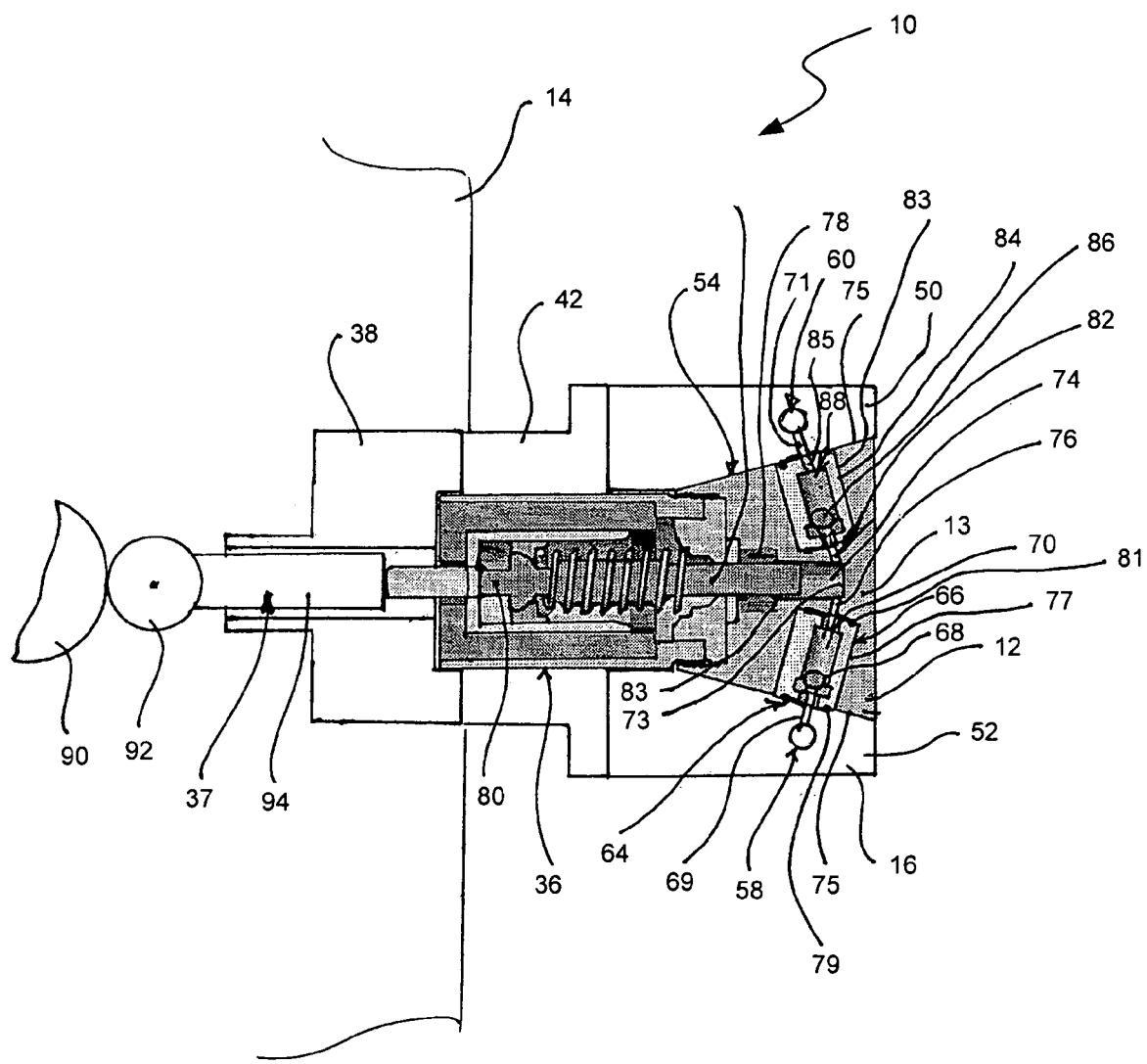
FIG. 6 is a cross-sectional view taken substantially along line 6—6 of FIG. 4 showing the pump head assembly and cooling jacket mounted to the pump module and coupled to a pump driver with a cam being shown.

FIG. 6 is a cross-sectional view taken substantially along line 6—6 of FIG. 4 showing the internal configuration of the pump system 10. As seen in FIGS. 4–6, the upper and lower wall portions 50 and 52 of the cooling jacket 16 each have an inner surface 75 that converge toward each other as the pump head receiving aperture 54 extends rearwardly toward the insulator block 42. The pump head assembly 12 has a pump head body 13 with generally wedge-shaped cross-sectional shape that matches the wedge shape of the pump head receiving aperture 54. The pump head body 13 of the illustrated embodiment is made of the same nickel-plated copper alley (i.e., CuTeP) that makes up the cooling jacket 16. When the pump head assembly 12 is inserted into the cooling jacket 16 and moved into an installed position, as shown, the pump head assembly is wedged into frictional engagement with the upper and lower wall portions 50 and 52 of the cooling jacket.

The pump head assembly 12 in the illustrated embodiment has two liquid flow paths therethrough: one for each cylinder that receives the reciprocating piston in the piston assembly 36. Only one flow path through the pump head assembly 12 is described in detail below, but the description is applicable to both flow paths. As best seen in FIG. 6, the pump head body 13 has a fluid inlet portion 64 sealably engaging the fluid outlet 69 in the cooling jacket's lower wall portion 52. The fluid inlet portion 64 contains a check valve assembly 66 that includes an internal check valve 68 configured to allow the liquid $CO_2$ to flow in only one direction through the pump head assembly 12.

In the illustrated embodiment, the check valve assembly 66 is a removable cartridge retained in an aperture 77 in the bottom side portion of the pump head body 13. The check valve assembly 66 is positioned to directly engage cooling jacket's lower wall portion 52 such that a small-bore fluid passageway 70 through the check valve assembly is coaxially aligned and sealably abutted with the respective fluid outlet 69 in the lower wall portion. This sealed, abutting arrangement allows for the chilled liquid $CO_2$ to flow smoothly through the cooling jacket's lower flow manifold 58 and the check valve assembly 66. In the illustrated embodiment, the check valve 68 in the inlet check valve assembly 66 is a high precision and high performance check valve having a sapphire seat and ruby ball that allows for very precise control of the flow of liquid $CO_2$ therethrough. In other embodiments, other high performance check valves can be used.

The check valve assembly 66 includes a slightly raised seal member 79 at its lower face portion. The seal member 79 sealably abuts with the cooling jacket's lower wall portion 52 to form a seal around the fluid outlet 69 that prevents leakage of the liquid $CO_2$ between the cooling jacket 16 and the valve assembly 66. Accordingly, the pump head assembly 12 does not require a separate mechanical connector to interconnect these two components through which the liquid $CO_2$ flows. When the wedge-shaped pump head assembly 12 is wedged into the installed position in the cooling jacket 16, the wedging forces sandwich the inlet check valve assembly 66 between the pump head body and the cooling jacket. As a result, the continuous fluid passageway between the cooling jacket and the pump head assembly are easily and precisely maintained.

In the illustrated embodiment, the liquid $CO_2$ flows into the pump head body 13 from the inlet check valve assembly 66 through an inlet passageway 76, and into an integral piston cylinder 74 formed by a blind hole coaxially aligned with the respective piston assembly 36. The end of the inlet check valve assembly 66 facing the cylinder 74 also has a seal member 81 that sealably engages the pump head body 13 around the inlet passageway 76 when the pump head assembly 12 is in the installed position.

The cylinder 74 has a closed end 73 adjacent to the inlet passageway 76 and an open end 83 opposite the closed end. A seal 78 is positioned around the reservoir's open end 83 and coaxially aligned with the cylinder 74. The cylinder's open end 83 receives an end portion of a piston rod 80 extending from the respective piston assembly 36. The piston rod 80 extends through the seal 78, such that a tight seal is formed against the piston as it reciprocates in the cylinder 74. In the illustrated embodiment, the piston rod 80 is a sapphire rod that exhibits exceptional performance characteristics, although other materials may be used. The seal 78 is a spring energized seal, such as an Omniseal™ from the Furon Company. Other seal materials, however, can be used as appropriate for the pumping conditions.

The piston assembly 36 is configured to drive the piston rod 80 in a reciprocal motion within the cylinder 74. As the piston rod 80 is drawn axially away from a top dead-center position closest to the cylinder's closed end 73, the piston travels through an aspiration stroke by moving toward a bottom dead-center position to create a lower pressure that draws the chilled liquid $CO_2$ into the cylinder. Accordingly, the cylinder 74 is at least partially filled with the liquid $CO_2$ during the aspiration stroke. Because the piston assembly 36 creates the lower pressure in the cylinder 74, the liquid $CO_2$ must be maintained at the low temperature (e.g., 0° C.) and high pressure so as to prevent liquid $CO_2$ from cavitating during the pumping process.

After the piston rod 80 completes the aspiration stroke, the piston travels from the bottom dead-center position back toward the cylinder's closed end 73, and the piston rod 80 travels through a discharge stroke, so as to drive the liquid $CO_2$ out of the cylinder 74. The inlet check valve 68 blocks the backflow of liquid $CO_2$ through the inlet check valve assembly 66 during this discharge stroke. The liquid $CO_2$ discharged from the cylinder 74 is forced through an outlet passageway 82 in the pump head body 13 opposite the inlet passageway 76. The outlet passageway 82 is in fluid communication with an outlet check valve assembly 84, which contains an outlet check valve 86. The outlet check valve 86 allows the liquid $CO_2$ to flow in only one direction: namely, away from the cylinder 74. The outlet check valve assembly 84 is tightly and sealably retained in an aperture 87 in the pump head body 13, similar to the aperture 77 that contains the inlet check valve assembly 66.

The outlet passageway 82 is coaxially aligned with the small-bore fluid passageway 85 extending through the outlet check valve assembly 84. The outlet check valve assembly 84 includes an end seal that sealably engages the pump head body 13 around the outlet passageway 82 when the pump head assembly 12 is wedged in the installed position in the cooling jacket 16. The opposite end of the outlet check valve assembly 84 also has a seal that sealably abuts the cooling jacket's upper wall portion 50 around one of the flow inlets 71. The outlet check valve assembly 84 defines a fluid outlet pathway 88 from the pump head assembly 12 into the upper manifold 60 through flow inlets 71 in the cooling jacket 16. The wedged configuration between the cooling jacket 16 and the pump head body 13 also securely and sealably sandwiches the outlet check valve assembly 84 between these components, so that the liquid $CO_2$ can smoothly flow through the pump head assembly 12 and the cooling jacket 16.

Figure 7:
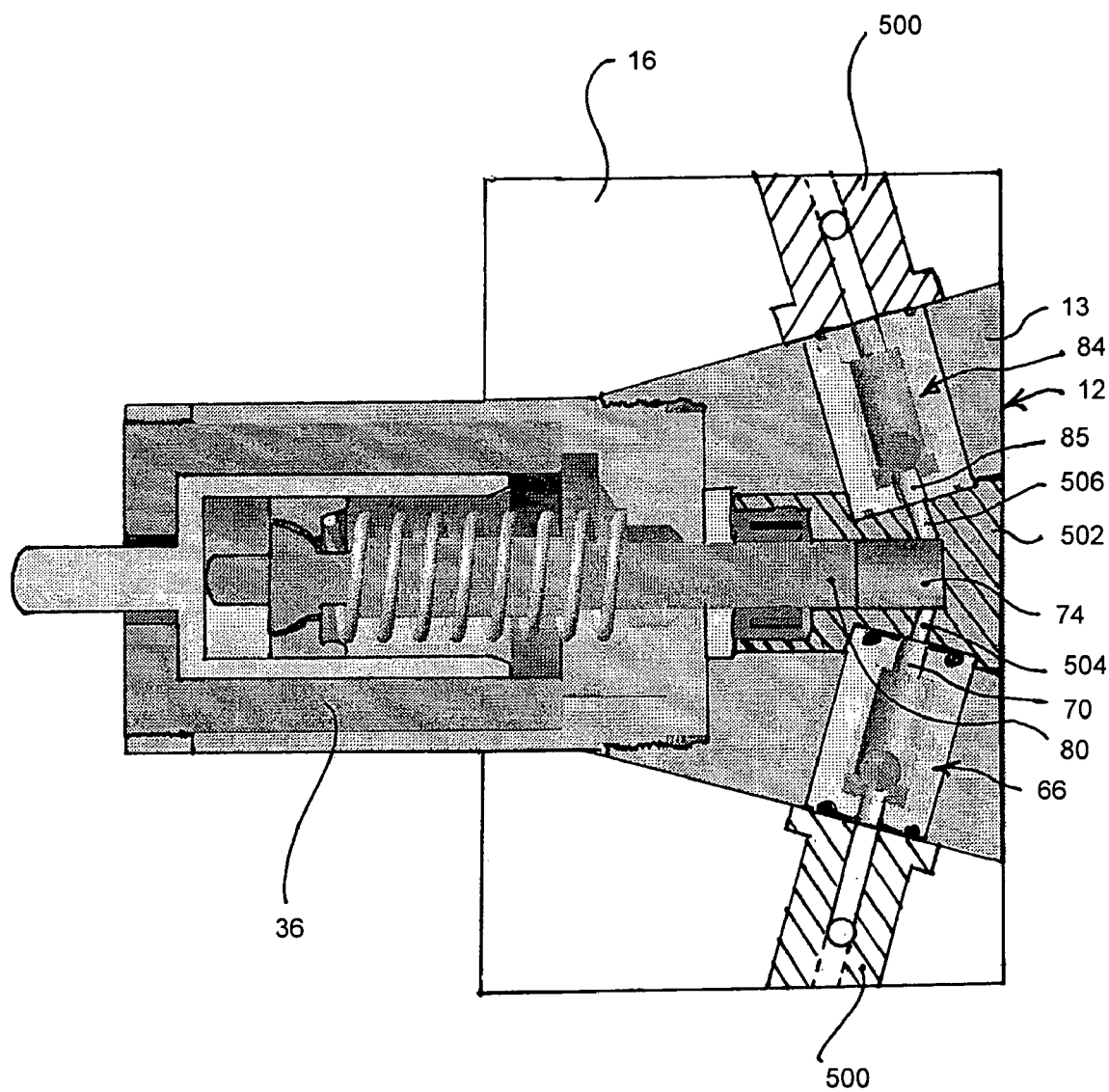
FIG. 7 is a cross-sectional view of a pump head assembly in an alternate embodiment of the invention.

FIG. 7 is a cross-sectional view of a pump head assembly 12 and cooling jacket 16 of an alternate embodiment. The pump head body 13 and the cooling jacket 16 in this alternate embodiment are made of aluminum. The aluminum provides very good thermal conductivity, although the aluminum does not react well with the liquid $CO_2$. Accordingly, the cooling jacket 16 is provided with stainless-steel inlet and outlet manifolds 500 securely received in elongated slots 402 formed in the cooling jacket's lower and upper wall portions 52 and 50. The stainless-steel manifolds 500 sealably engage the inlet and outlet check valve assemblies 66 and 84. Therefore, the stainless-steel manifolds 500 define the fluid path through the cooling jacket 16 so that the liquid $CO_2$ does not come into contact with the aluminum material in the cooling jacket 16.

The pump head body 13 of this illustrated alternate embodiment has an aperture that contains a stainless-steel central insert 502 axially aligned with the respective piston assembly 36. The central insert 502 has the blind-hole cylinder 74 formed therein to receive the piston rod 80 of the respective piston assembly 36. The cylinder 74 in the central insert 502 is in fluid communication with an inlet passageway 504 formed in the insert. The inlet passageway 504 is in direct fluid communication with the fluid passageway 70 through the inlet check valve assembly 66 to carry the flow into the reservoir 74. The cylinder 74 is also in fluid communication with an outlet passageway 506 formed in the central insert 502. The outlet passageway 506 is in direct fluid communication with the fluid passageway 85 through the outlet check valve assembly 84. As a result, the liquid $CO_2$ flows from the stainless steel inlet manifold 500 directly into the inlet check valve assembly 66, through the stainless steel central insert 502, into the outlet check valve assembly 84, and directly into the stainless steel outlet manifold in the cooling jacket 16. Therefore, the liquid $CO_2$ will always be out of engagement with any aluminum as the flow moves through the pump head assembly 12 and the cooling jacket 16. Although the illustrated embodiment provides stainless-steel as the material that contacts the flow of liquid $CO_2$, other suitable materials can be used as appropriate for the characteristics of the particular fluid flow.

As seen in FIGS. 1 and 4, access to the pump head assembly 12 from the front of the pump system 10 is not obstructed by other components in the system. When components in the pump system 10, such as the inlet or outlet check valve assemblies 66 and 84, the seals 78, or the piston assemblies 36, need routine maintenance or other servicing, the pump head assembly 12 can be easily removed by sliding the pump head assembly out of the unobstructed front side of the cooling jacket 16.

In one embodiment for the pumping system 10, the cooling jacket 16 and chilled pump an insulative material can removably cover head assembly 12. The insulative material helps in minimizing the buildup of frost or ice on the chilled pump head assemblies and cooling jacket during operation of the pump system. The insulative material can be releasably held in place by a hook-and-loop type configuration or other suitable removable connection system that allows the insulation to remain in place over the pump head assembly 12 and cooling jacket 16 while being easily and quickly removable for direct access to the pump head assembly 12. In one embodiment, the insulative material includes a front cover panel that can be easily removed to expose the pump head assembly 12. In other embodiments, other materials or systems can be used to assist in minimizing frost and ice buildup while minimizing the interference with access and serviceability of the pump head assembly 12.

In the illustrated embodiment of FIGS. 1 and 5, the pump head assembly 12 is securely retained in the installed position by a retaining screw 90 extending through an aperture in the pump head assembly and engaging the back wall portion of the cooling jacket. After the retaining screw 90 is removed, the pump head assembly 12 is dislodged from its wedged position by rotating a jack screw 93 or the like extending through a portion of the pump head body. Once dislodged, the pump head assembly 12 is removed from the cooling jacket 16 without having to separately break any mechanical connections between fluid lines or the like. New check valve assemblies then can be installed quickly into the pump head assembly, or a new pump head assembly can be quickly installed into the cooling jacket.

The new pump head assembly is secured in the installed position with the retaining screw 90, thereby automatically aligning the fluid passageways that allow for the flow of the liquid $CO_2$ through the pump head assembly as discussed above. The removed liquid pump head assembly 12 can then be repaired or serviced as convenient while the pump system 10 remains operational, thereby greatly minimizing the downtime of the pump system.

In the illustrated embodiment shown in FIG. 6, the pump system 10 includes a dual-piston pump assembly with two piston assemblies 36 driven by two pump drivers 37 coupled to a stepper motor (not shown). The pump drivers 37 in the illustrated embodiment are configured so that the piston assemblies 36 are operated to alternatively deliver the liquid $CO_2$ 180° out of phase with each other, so as to provide a substantially continuous and steady flow of the liquid $CO_2$ through the pump head assembly 12 and along the fluid system. Each pump driver 37 has a cam 90 that engages a cam follower 92 connected to a reciprocating plunger 94. The plunger 94 is in contact with a piston tail guide that engages the end of the elongated piston rod 80 of the piston assembly 36. The other end of the piston rod 80 extends through the seal ring 78 and into the cylinder 74, as discussed above. Each cam 90 rotates about a central axis and causes the cam follower 92 and plunger 94 to move axially in a reciprocating motion. This reciprocating motion causes the piston rod 80 to move along the discharge and aspiration strokes. A spring 98 or other biasing member is positioned between the cam follower 92 and the piston assembly 36 and biases the plunger 94, and thus, the piston rod 80, toward bottom dead-center, which is the beginning of the aspiration stroke.

The cam 90 is a three-stage cam, shaped and sized so the discharge stroke has an initial compression portion that occurs when the plunger 94 and piston rod 80 move from bottom dead-center a selected distance toward top dead-center. During this compression portion, the liquid $CO_2$ in the cylinder 74 is fully compressed before actually being discharged out of the reservoir through the outlet check valve assembly 84. The compression portion of the discharge stroke is followed by a fluid delivery portion, wherein the piston rod 80 drives the compressed liquid $CO_2$ out of the reservoir 74 through the outlet check valve assembly 84 and through the upper wall portion 50 of the cooling jacket 16. After the plunger 94 and the piston rod 80 reach top dead-center, further rotation of the cam 90 causes the piston rod to move back toward bottom dead-center along the aspiration stroke to draw the liquid $CO_2$ into the reservoir 74.

Figure 8:
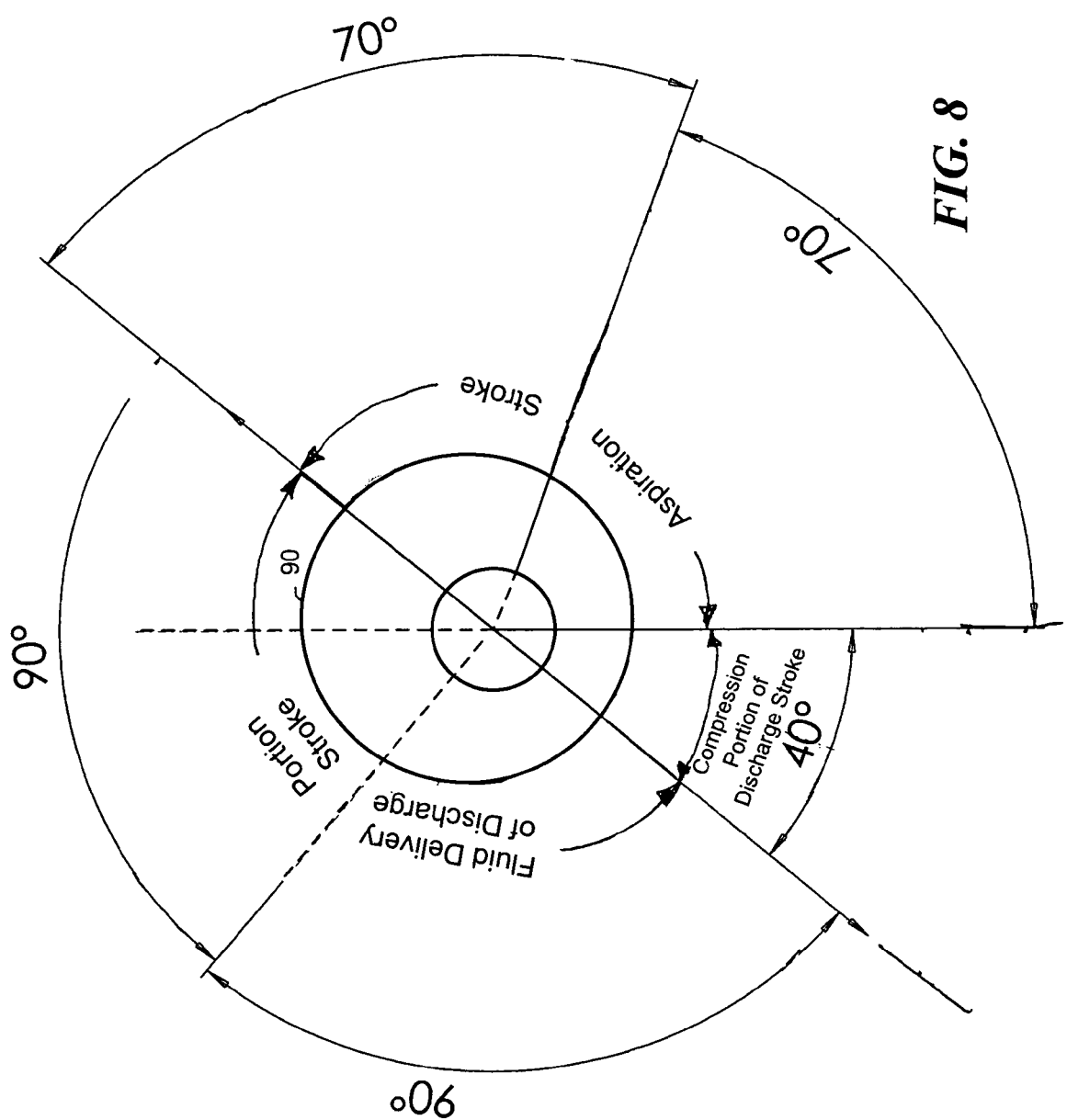
FIG. 8 is an enlarged side elevation view of the cam of FIG. 6.

FIG. 8 is a side elevation view of the three-stage cam 90 in accordance with an embodiment of the invention. The cam 90 is shaped and sized so the plunger 94 and piston rod 80 move faster along the compression portion of the discharge stroke and slower along the fluid delivery portion for controlled delivery of the liquid $CO_2$ out of the pump head assembly 12. In one embodiment, the fluid compression portion of the discharge stroke is approximately 30 percent of the full discharge stroke. The fluid delivery portion is approximately 70 percent of the full discharge stroke. The cam 90 is shaped and sized so that the compression portion of the discharge stroke occurs upon rotation of the cam through approximately 30°–50°, and the fluid delivery portion of the discharge stroke occurs upon rotation of the cam 90 through approximately 170°–190°. The full aspiration stroke occurs upon rotation of the cam 90 through approximately 130°–150°. In one embodiment, the compression portion of the discharge stroke is completed upon rotation of the cam 90 through approximately 40°, and the fluid delivery portion of the discharge stroke is completed upon rotation of the cam 90 through approximately 180°. The aspiration stroke is completed upon rotation of the cam 90 through approximately 140°.

Figure 9:
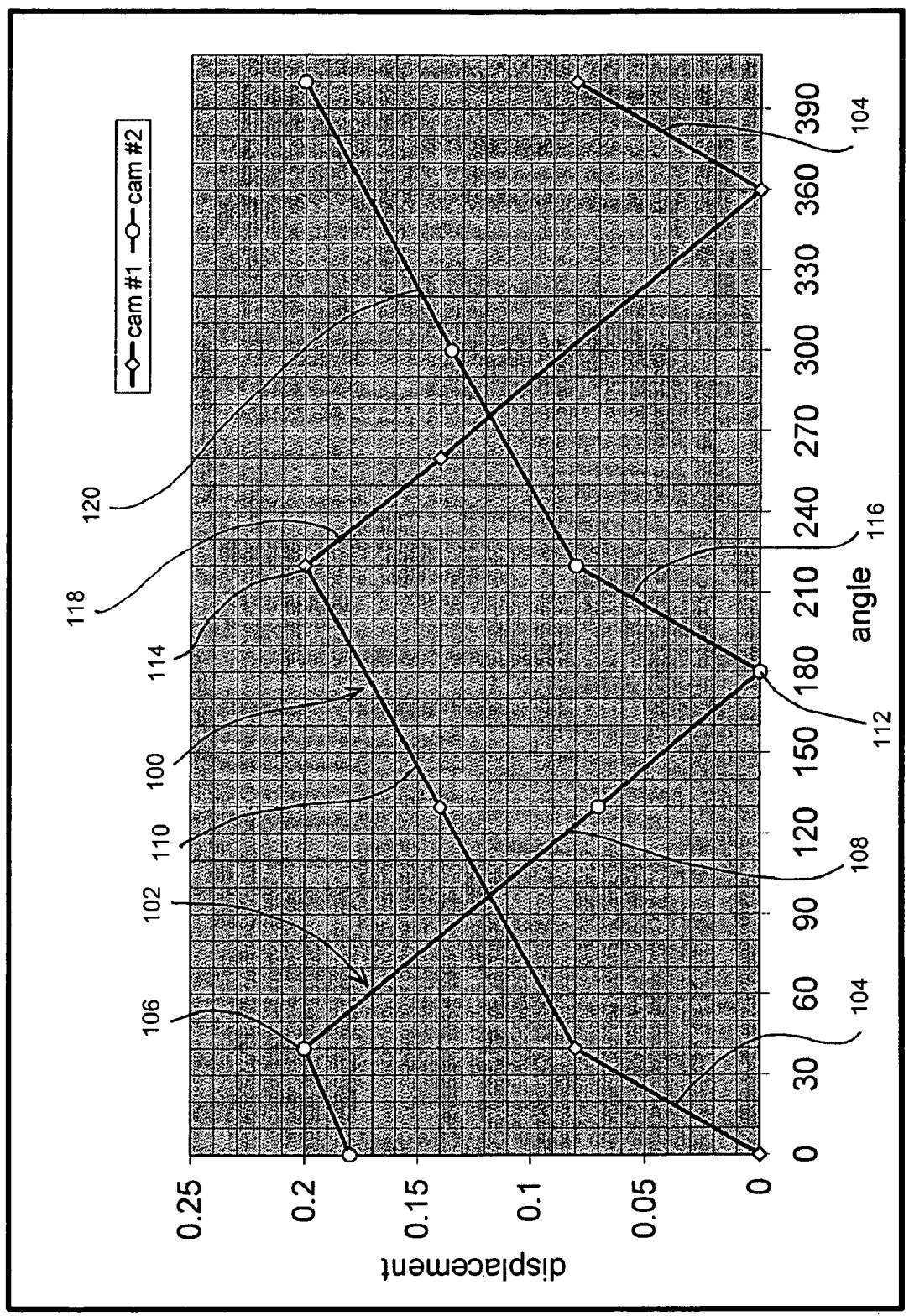
FIG. 9 is a graph showing the stroke patterns of the pump system upon rotation of two of the cams of FIG. 8.

The cams 90 are matched and arranged relative to each other so that the piston assemblies 36 provide alternating pump strokes. FIG. 9 is a schematic graph showing the aspiration and discharge strokes for a pair of matched cams 90 in one embodiment of the invention. The line identified by reference number 100 represents the rotation of a first cam, and the line identified by reference number 102 represents the rotation of a second cam. As can be seen, the first cam substantially finishes the compression portion 104 of the discharge stroke when the second cam reaches top dead-center 106 and begins its aspiration stroke 108. The first cam undergoes the fluid delivery portion 110 of the discharge stroke as the second cam performs its entire aspiration stroke 108 and reaches bottom dead-center 112. Before the first cam reaches top dead-center 114, the second cam moves from bottom dead-center 112 and begins its compression portion 116 of the discharge stroke. As soon as the first cam reaches top dead-center 114 and begins its aspiration stroke 118, the second cam begins its fluid delivery portion 120 of the discharge stroke.

The cam configurations discussed above were selected for pumping liquid $CO_2$ at approximately 0° C. If the aspiration stroke is too quick, the pressure in the reservoir 74 will drop too much and could cause cavitation in the liquid $CO_2$ being drawn into the reservoir. If the compression portion of the discharge stroke is too fast, excess pressure may be generated in the reservoir 74 and prematurely initiate the fluid delivery through the outlet check valve assembly 84, which could cause an undesirable pulsing within the fluid lines. While the cams 90 of the illustrated embodiment are configured to provide the portions of the discharge and aspiration strokes at the rates discussed above for pumping liquid $CO_2$, other three-stage cam configurations and stroke timing can be used as is appropriate for the compressive liquid being pumped with the pump system 10.

Figure 10:
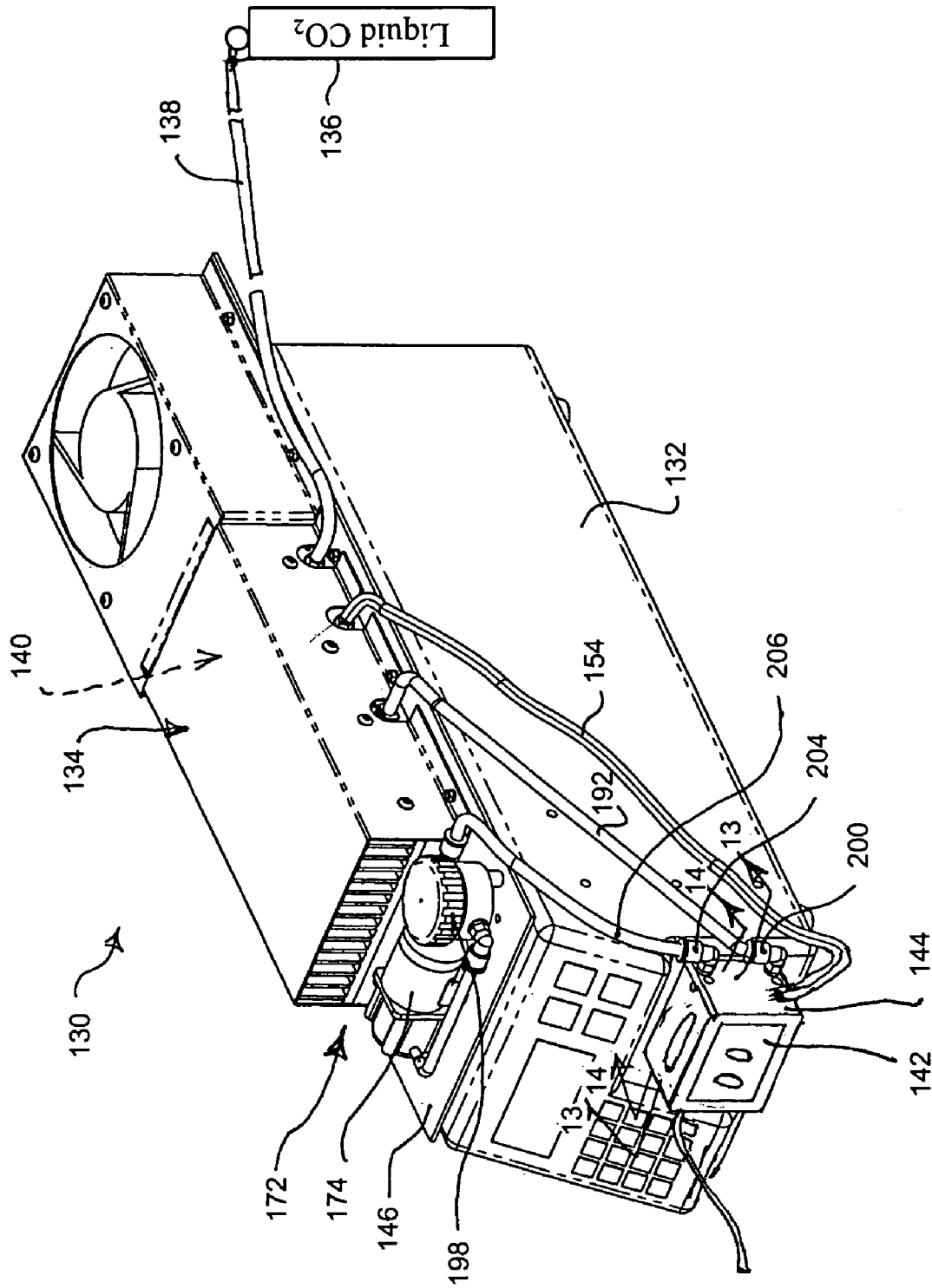
FIG. 10 is a front isometric view of a pump system for pumping liquefied gas in accordance with an alternate embodiment of the invention, with a chiller assembly shown mounted on the top of a pump module.

FIG. 10 is a front isometric view of a pump system 130 in accordance with an alternate embodiment of the present invention. The pump system 130 includes a pump module 132 having a heat exchanger assembly 134 mounted to its top portion. The heat exchanger assembly 134 is coupled to a liquid $CO_2$ source 136 via insulated small-bore fluid lines 138. The liquid $CO_2$ flows from the source 136 through the fluid lines 138 into a chiller 140 that cools the liquid $CO_2$. The liquid $CO_2$ is then drawn via a fluid line to the pump head assembly 142 through the cooling jacket 144. The pump head assembly 142 has substantially the same configuration as the pump head assembly 12 discussed above. The cooling jacket 144 also has substantially the same configuration as the cooling jacket 16 discussed above, such that only the differences in these components will be discussed in greater detail below.

The heat exchanger assembly 134 is positioned on top of the pump module 132 in close proximity to the pump head assembly 142 and cooling jacket 144, but positioned so as to avoid obstructing access to the pump head assembly through the front of the cooling jacket. Accordingly, the pump head assembly 142 is easily accessible and can be quickly removed and serviced or replaced with a backup pump head assembly so as to minimize the downtime of the pump system 130. The heat exchanger assembly 134 is configured to maintain the liquid $CO_2$ at approximately 0° C. during the entire pumping process so as to maintain a consistent flow of liquid $CO_2$ through the fluid lines 108.

Figure 11:
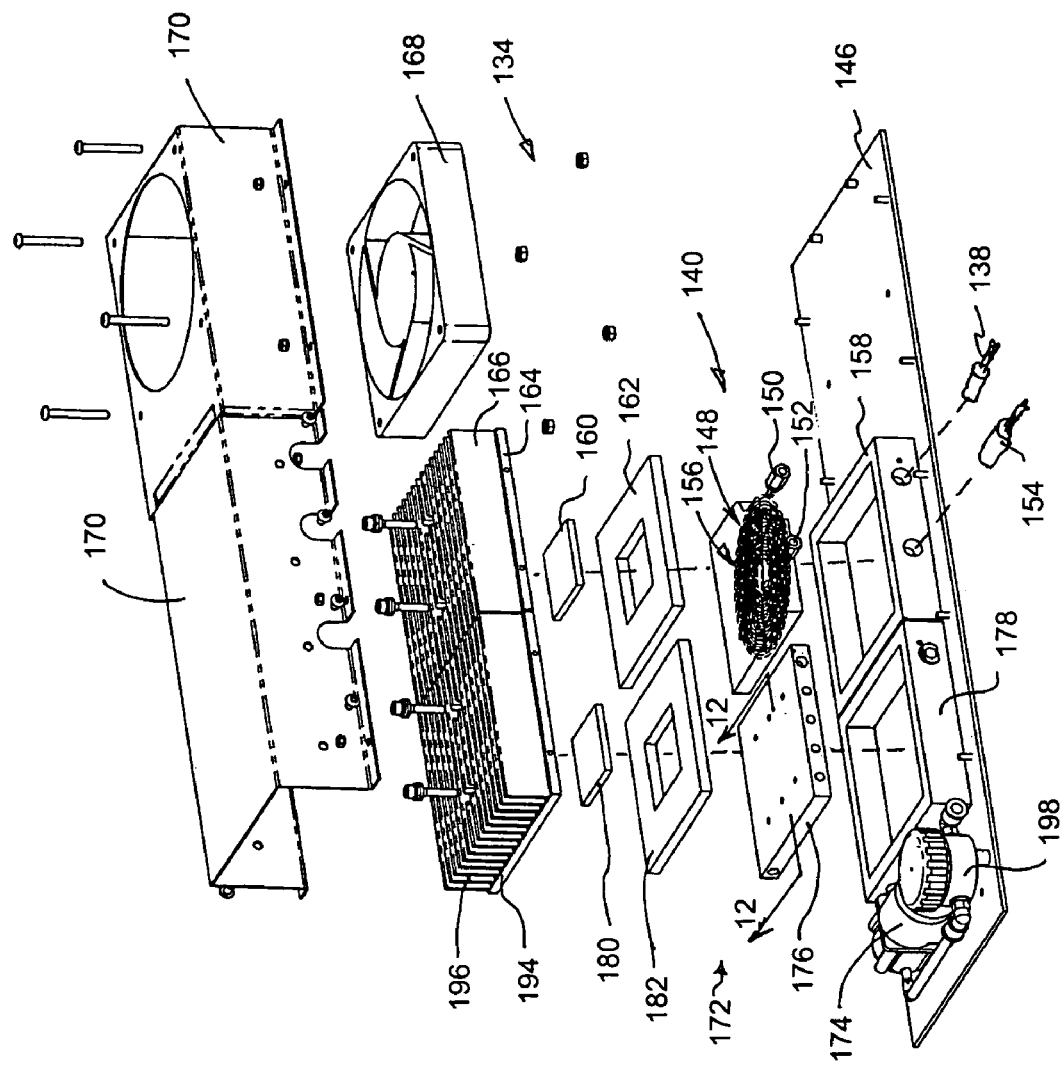
FIG. 11 is an enlarged, partially exploded, top isometric view of the chiller assembly of FIG. 10 shown removed from the pump module.

FIG. 11 is an exploded, enlarged isometric view of the heat exchanger assembly 134 shown removed from the top of the pump module. The heat exchanger assembly 134 includes a mounting plate 146 that supports the chiller 140. The chiller 140 includes a cooling coil 148 constructed of small-bore tubing 156 and an inlet fitting 150 that releasably attaches to the fluid line 138 (FIG. 10) coupled to the liquid $CO_2$ source 136 (FIG. 10). The cooling coil 148 also includes an outlet fitting 152 connected to a fluid line 154 connected to the cooling jacket 144 (FIG. 10).

The liquid $CO_2$ flows from the inlet fitting 150, through the small-bore tubing 156 around the cooling coil 148, and out to the outlet fitting 152. The cooling coil 148 is contained in an insulative housing 158 mounted to the mounting plate 146. A thermoelectric cooler 160 is positioned on top of the cooling coil 148 and held in place by a support frame 162. The thermoelectric cooler 160 of the illustrated embodiment is a selected Peltier cooler that maintains the liquid $CO_2$ at approximately 0° C. Other thermoelectric coolers can be used, or the flow of liquefied gas can be maintained at other temperatures as desired, by controlling the thermoelectric cooler on the cooling coil.

The thermoelectric cooler 160 and support frame 162 are sandwiched against the cooling coil 148 by a heat sink 164. The heat sink 164 has a plurality of elongated fins 166 that use convection to draw heat away from the heat exchanger and the thermoelectric chiller 160. A fan 168 is mounted to the mounting plate 146 adjacent to the heat sink 164 so as to blow air across the fins 166 to facilitate the heat removal by convection. The heat sink 164 and the fan 168 are covered by protective shrouds 170 that mount to the mounting plate 146.

The pump head assembly 142 (FIG. 10) is chilled by a closed-loop, recirculating cooling bath system 172. In one embodiment, the cooling bath fluid is methanol, although other cooling bath fluids, such as ethylene glycol, could be used. The cooling bath system 172 is also mounted to the mounting plate 146 adjacent to the chiller 140. The cooling bath system 172, as best seen in FIG. 11, includes a recirculating pump 174 that pumps the cooling bath fluid into a chiller plate 176 contained in a housing 178 mounted to the mounting plate 146. A thermoelectric cooler 180, such as a Peltier cooler, is mounted on top of the chiller plate 176 within a support frame 182 to cool the cooling bath fluid to approximately 0° C. as it flows through the chiller plate.

Figure 12:
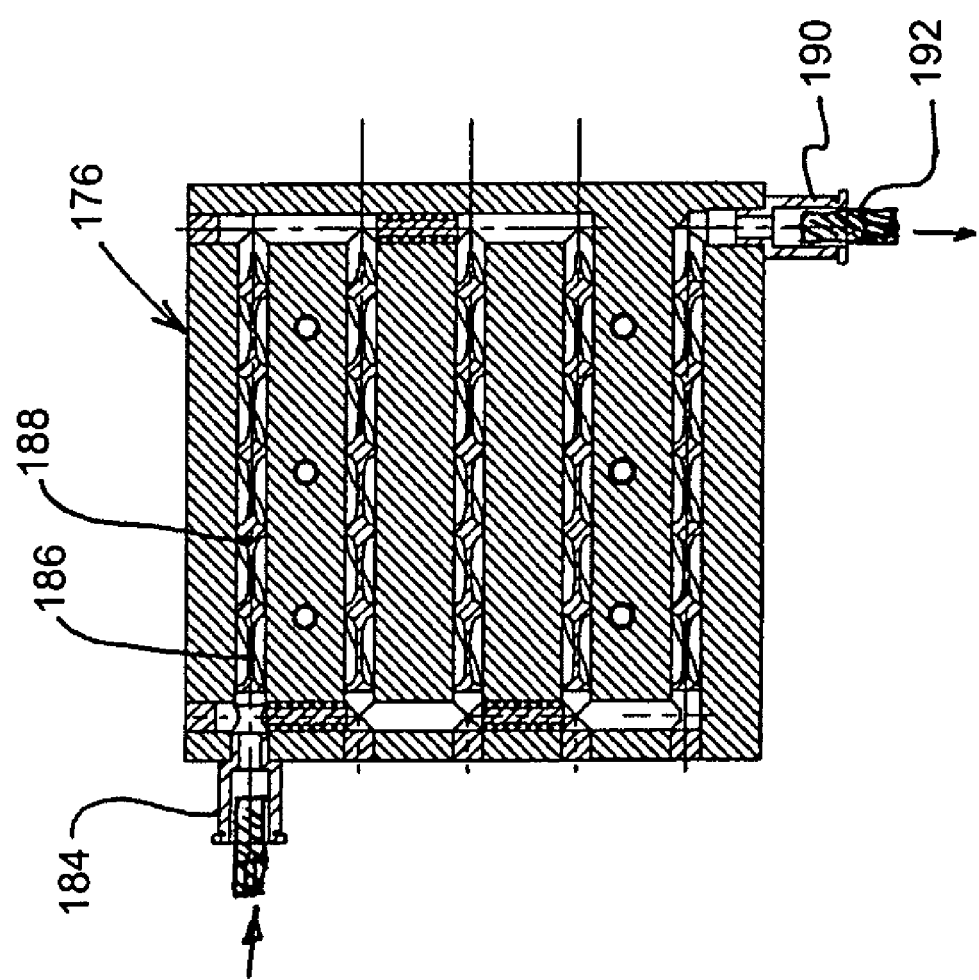
FIG. 12 is an enlarged cross-sectional view taken substantially along line 12—12 of FIG. 11 showing a cooling plate of the heat exchanger system.

In the illustrated embodiment, the recirculating pump 174 is also coupled to a reservoir/expansion chamber 198 adapted to compensate for changes in the volume of the cooling bath fluid due to temperature changes in the cooling bath fluid. The reservoir/expansion chamber 198 of the illustrated embodiment includes a rolling diaphragm that acts to compensate for change of fluid volume FIG. 12 is an enlarged cross-sectional view of the chiller plate 176 taken substantially along line 12—12 of FIG. 11. The chiller plate 176 includes an inlet 184 in fluid communication with the chiller pump 174 and adapted to receive the flow of cooling bath fluid. The inlet 184 is in fluid communication with a plurality of channels 186 formed within the chiller plate 176. These channels 186 define a tortuous pathway to maximize the chilling of the cooling bath fluid as it passes through the chiller plate 176. A plurality of turbulators 188 are positioned in the chiller plate's passageways 186. The turbulators 188 create turbulent flow of the cooling bath fluid as it flow through passageways 186, thereby enhancing the cooling of the fluid. In the illustrated embodiment, the turbulators 188 are lengths of spiraled aluminum shaped and sized to rotate within the passageways 186 as the cooling fluid flows past the turbulators. The chiller plate 176 includes an outlet fitting 190 coupled to the passageways 186 and connected to an outlet fluid line 192 that carries the chilled cooling bath fluid away from the chiller plate. The outlet line 192 is connected at its opposite end to the cooling jacket 144 (FIG. 10).

As best seen in FIG. 11, the recirculating cooling bath system 172 also includes a heat sink 194 that sandwiches the thermoelectric cooler 180 and the mounting frame 182 against the top of the chiller plate 176. The heat sink 194 includes a plurality of fins 196 adjacent and generally aligned with the fins 166 of the heat sink 164 coupled to the cooling coil 148. The fan 168 blows air across both sets of fins 166 and 196 to draw heat away from the respective heat sinks 164 and 194. The protective shroud 170 covers both the heat sinks 164 and 194, as well as the other components of the recirculating cooling bath system, with the exception of the chiller pump 174.

As best seen in FIG. 10, the cooling jacket 144 includes an inlet fitting 200 coupled to the outlet line 192 of the recirculating cooling bath system 172. The chilled cooling bath fluid flows through the inlet fitting 200 through channels in the cooling jacket 144, and out an outlet fitting 204. The outlet fitting 204 is coupled to an outlet line 206 that is, in turn, in fluid communication with the reservoir/expression chamber 198 and then the chiller pump 174 so as to create the closed loop for the recirculating cooling bath system. After the cooling bath fluid flows into the cooling jacket 144, the fluid flows through a plurality of tortuous fluid channels within the cooling jacket, thereby chilling the cooling jacket to approximately 0° C. or other selected temperature.

Figure 14:
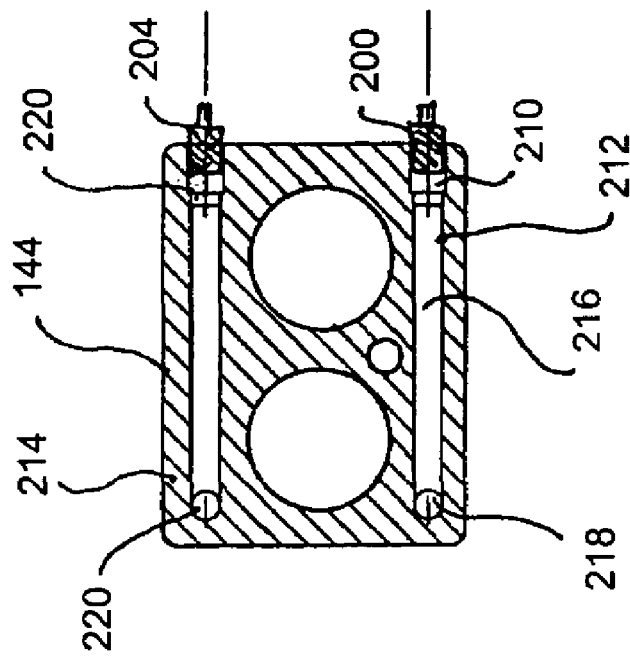
FIG. 14 is an enlarged cross-sectional view taken substantially along line 14—14 of FIG. 10 showing additional chilling-fluid pathways in the cooling jacket.
Figure 13:
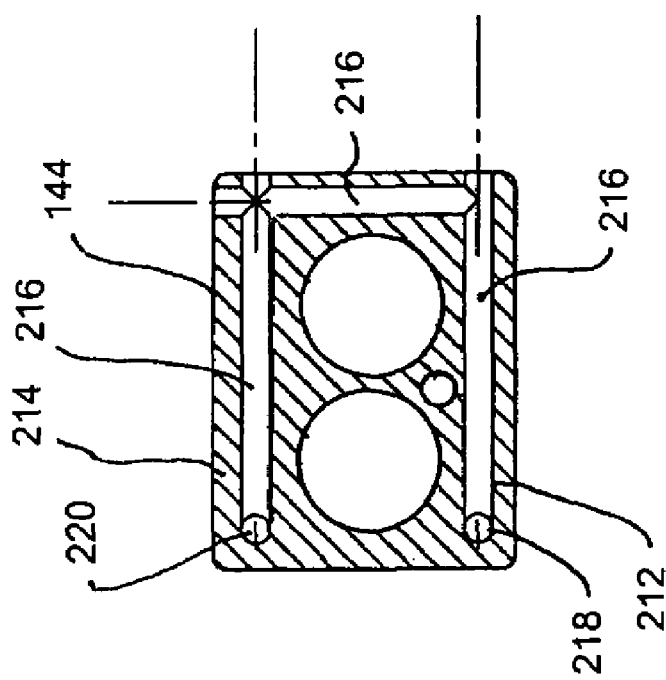
FIG. 13 is an enlarged cross-sectional view taken substantially along line 13—13 of FIG. 10 showing chilling-fluid pathways in the cooling jacket.

FIG. 13 is an enlarged cross-sectional view through the cooling jacket 144 taken substantially along the lines of 13—13 of FIG. 10. FIG. 14 is an enlarged cross-sectional view of the cooling jacket 144 taken substantially along line 14—14 of FIG. 10. The cooling jacket 144 has an inlet 210 that connects with the inlet fitting 200 and that communicates with a plurality of internal passageways 212 formed by a series of interconnected bores formed in the back-wall portion 214 of the cooling jacket 144. A series of horizontal bores 216 are connected at one end by a transverse bore 218 on one side of the back-wall portion 214 and a second transverse bore 220 on the opposite side of the body. The bores 216, 218, and 220 form a substantially continuous serpentine passageway extending back and forth across the back-wall portion 214 of the cooling jacket 144 between the inlet 210 and an outlet 222 in fluid connection with the outlet fitting 204 on the cooling jacket. Accordingly, the chilled cooling bath liquid is pumped through the continuous serpentine pathways of the cooling jacket 144 so as to continuously chill the pump head assembly 142 (FIG. 10) during the pumping operation.

Figure 15:
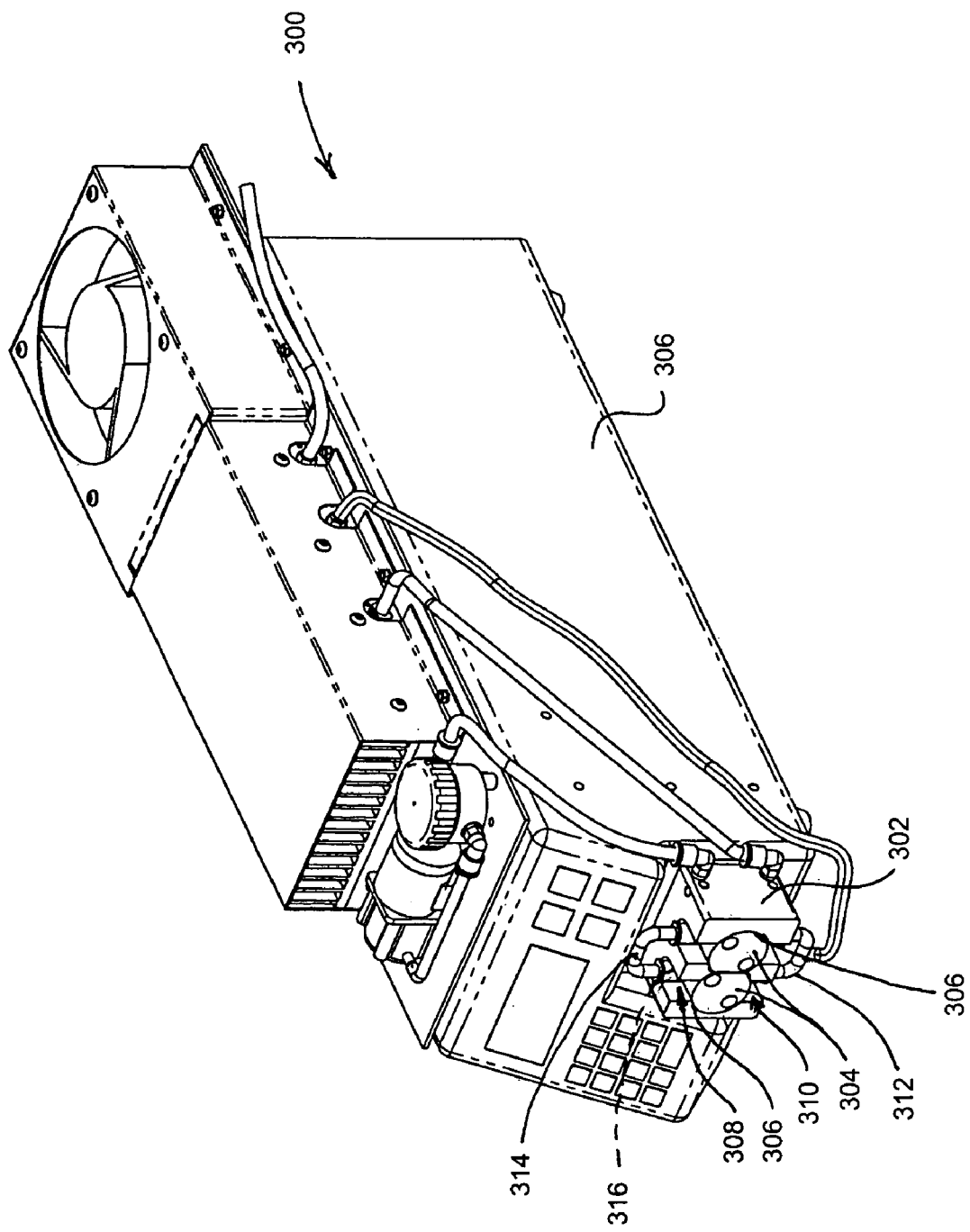
FIG. 15 is a front isometric view of a liquefied-gas pumping system in accordance with another alternate embodiment of the present invention.

FIG. 15 is a front isometric view of a pump system 300 in accordance with another alternate embodiment of the present invention. This embodiment is similar to the pump system 100 discussed above, except for the configuration of the cooling jacket 302 and the dual pump head assemblies 304 mounted to the front portion of the pump module 305. In this embodiment, the pump module 305 is constructed with two pistons driven by a step-motor through cam mechanisms, as discussed above. The pump head assemblies 304 are received in a pair of generally cylindrical receiving recesses 306 formed in the front of the cooling jacket 302. The recesses 306 are formed to completely receive and encompass the pump head assemblies 304 so as to be fully chilled. Upper and lower slots 308 and 310 are provided in the cooling jacket 302 and communicate with the recesses 306 so as to provide space for inlet lines 312 and outlet lines 314 to the pump head assemblies 304. The liquid $CO_2$ flowing through the inlet lines 312 pass through a one-way check valve coupled to each one of the pump heads 304. The outlet fluid lines 314 are also coupled to one-way check valves 316 so as to maintain a single direction of fluid flow through the pump head assemblies and to prevent back flow. The pump heads 304 are configured to provide a substantially continuous flow of the liquid $CO_2$ along the system lines while maintaining easy accessibility and serviceability of the pump head assemblies of the pump system 300.

The embodiment illustrated in FIG. 15 utilizes the heat exchanger system 134 and the recirculating cooling bath system to chill the cooling jacket 172 as discussed above. In an alternate embodiment, the chiller assembly 22, as discussed above and illustrated in FIG. 1, could be connected to the side of the cooling jacket to provide the cooling functions.

Figure 16:
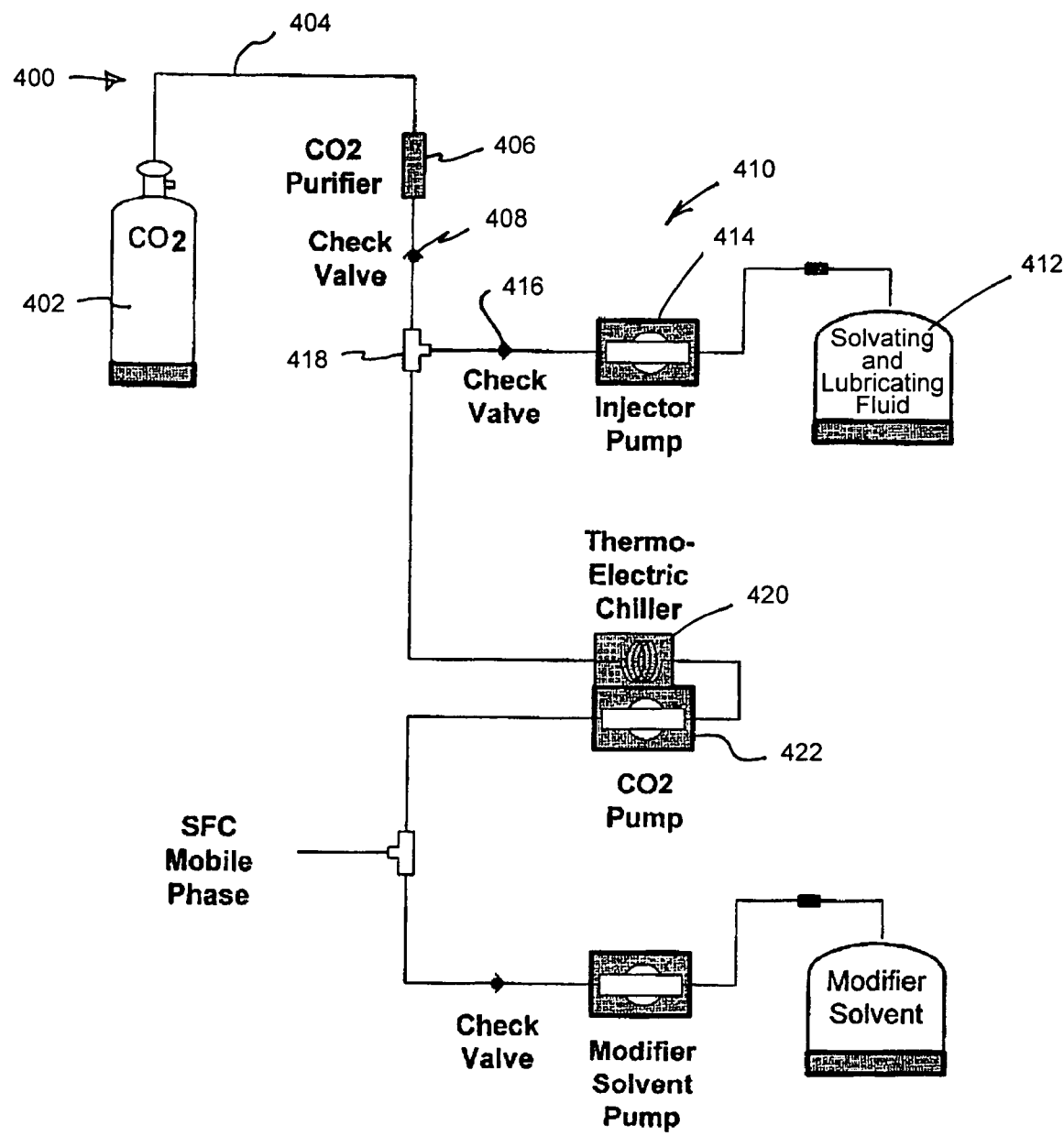
FIG. 16 is a partial schematic view of an SFC system using liquid $CO_2$ as a carrier fluid, with a purifier and a solvating-liquid pump upstream from the liquid $CO_2$ pump in accordance with an alternate embodiment of the present invention.

FIG. 16 is a schematic view of a fluid pumping system 400 that pumps liquid $CO_2$ from a $CO_2$ source 402 through small-bore fluid lines 404. In one embodiment, the pump system is used in an SFC or HPLC high throughput purification system. Liquid $CO_2$ is commercially available in different grades having different levels of purity. The highest grade liquid $CO_2$ contains very few impurities that would adversely impact the pump systems for high pressure, low temperature pumping of the liquefied gas. The high grade liquid $CO_2$, however, is more expensive than the lower grade liquid $CO_2$, which contains more impurities. Pumping the liquid $CO_2$ containing some impurities through the pump systems discussed above may negatively impact the operational life of the check valve assemblies, the seals, and other components in the $CO_2$ pump system. The liquefied gas pumping system 400 of the illustrated embodiment is useable to provide, among other things, increased service life of the components in the liquid $CO_2$ pumping system.

In the illustrated liquid $CO_2$ pumping system 400, a liquid $CO_2$ purifier 406 is connected to the fluid lines 404 downstream of the liquid $CO_2$ source 402 so as to remove some of the contaminants in the flow of liquid $CO_2$. The purifier 406 is effective to remove a significant level of contaminants from the liquid $CO_2$, although most purifiers do not purify the liquid $CO_2$ completely. In one embodiment, the purifier 406 is a P700-2 liquid $CO_2$ purifier manufactured by VICI Matson, Inc. A check valve 408 is provided downstream from the purifier 406 to prevent a back flow of liquid $CO_2$ through the purifier. A lubricating and solvating liquid injection system 410 is coupled to the fluid lines 404 downstream of the check valve 408.

The injection system 410 of the illustrated embodiment includes a source 412 of lubricating and solvating liquid coupled to an injector pump 414. The injector pump 414 is adapted to draw a selected amount of the lubricating and solvating liquid from the source 412 and pump it through a check valve 416 and to an injector fitting 418 coupled to the fluid lines 304 downstream of the $CO_2$ purifier. Accordingly, the lubricating and solvating liquid is introduced into the flow of liquid $CO_2$ or other liquefied gas.

The lubricating and solvating liquid is pumped into the liquid $CO_2$ stream at a flow rate of approximately 0.2 milliliters per minute. The liquid $CO_2$ stream in this embodiment flows at a nominal rate of 8 milliliters per minute, such that the solvating liquid represents 2.5 percent of the overall flow of fluid through the fluid lines 304. Other embodiments inject the lubricating and solvating liquid at greater or lessor percentages of the overall flow stream than 2.5 percent. In the illustrated embodiment, the lubricating and solvating liquid is methanol. In alternate embodiments, other liquids can be used to provide the lubricating and solvating aspects to the liquid $CO_2$ or other liquefied gas. In other alternate embodiments, one liquid can be used and introduced into the flow of liquefied gas to provide the solvating characteristics, and another liquid can be introduced to provide the lubricating characteristics.

The lubricating and solvating liquid and liquid $CO_2$ form a mixture that flows through the system lines 404, through a chiller system 420, such as the chiller systems discussed above. The mixture also flows through the liquid $CO_2$ or other liquefied gas pumping system, as discussed above. The mixture of lubricating and solvating liquid flowing through the pump head assemblies provides a lubricating action and a solvating action to the check valve assemblies and seals in the $CO_2$ pump, thereby reducing the negative effects of the contaminants in the liquid $CO_2$ in terms of wearing on the check valve assemblies, seals, and other components in the pump system exposed to this fluid flow. While the check valve assemblies in the embodiments discussed above can be easily removed and replaced from the pump system, failed seals typically will require replacement, which can add to the cost of operating the liquid $CO_2$ pump over time. The longer the seal life can be maintained, the more economical the pump system can be over its lifetime.

Figure 17:
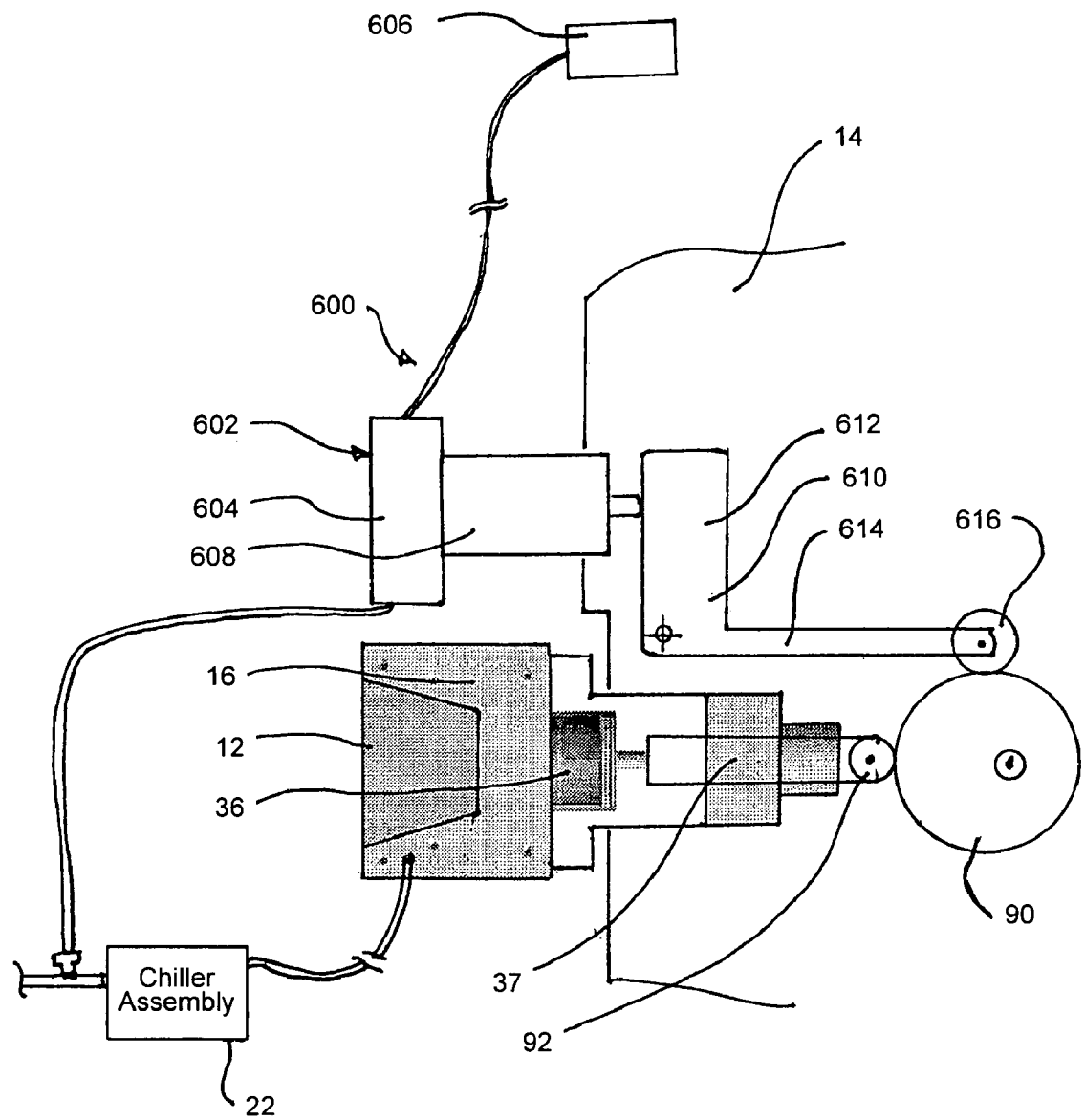
FIG. 17 is a partial side elevation view of a pump system including a lubricating/solvating pump assembly in accordance with an alternate embodiment of the invention.

In one embodiment, the injection system 410 is separate from the pump module 14 and is connected to the fluid lines upstream from the chiller system 402. FIG. 17 is a partial side elevation view of an injection system 600 coupled to the pump module 14 and the three-stage cam 90 in accordance with an alternate embodiment. The injection system 600 includes an injector pump assembly 602 with an injection pump head 604 in fluid connection with the source 606 of lubricating and solvating fluid. The injector pump assembly 602 has a piston assembly 608 operatively connected at one end to the injector pump head 604, such that activation of the piston assembly 608 causes the lubricating and solvating fluid to be pumped through the injector pump head.

The piston assembly 608 of the illustrated embodiment is mounted in the pump module 14 generally adjacent to the piston assembly 36 discussed above. The piston assembly 608 is operatively connected to a pivotal bell crank 610 that acts as a piston driver. The bell crank 610 is an L-shaped member with one leg 612 that engages the end of the piston assembly 608. The other leg 614 carries a cam follower 616 on the leg's free end. The cam follower 616 engages the same cam 90 that drives the piston assembly 36. Accordingly, the injection system 600 uses the same stepper motor and cam 90 for simultaneous operation with the liquid $CO_2$ pump assembly. The delivery timing and volume of lubricating and solvating fluid can be controlled by selecting the appropriately sized bell crank 610 and the pivot point of the bell crank relative to the piston assembly 608.

In the illustrated embodiment, the injector pump head 604 has a fluid outlet line 618 that connects to the fluid system lines 404 just upstream of the chiller assembly 22 (shown schematically). The lubricating and solvating liquid enters the flow of liquid $CO_2$ just before it enters the chiller assembly 22. The lubricating and solvating liquid fully mixes with the liquid $CO_2$ as the flow moves through the chilling coil in the chiller assembly 22. Accordingly, pump head assembly 12 receives the mixture of liquid $CO_2$ and the lubricating and solvating fluid so, the check valve assemblies and the seals in the pump head assembly are lubricated, and subject to less contamination during operation of the pump assembly.

Although specific embodiments of, and examples for, the present invention are described herein for illustrative purposes, various equivalent modifications can be made without departing from the spirit and scope of the invention, as will be recognized by those skilled in the relevant art. The teachings provided herein of the present invention can be applied to pumping systems for pumping compressible fluids, including liquefied gases, not necessarily to the exemplary liquid $CO_2$ pumping system described above.

In general, in the following claims, the terms used should not be construed to limit the invention to the specific embodiments disclosed in the specification and the claims, but should be construed to include all liquefied gas and/or compressible liquid pumping systems that operate in accordance with the claims to provide pumping systems and methods for pumping compressible liquids. From the foregoing, it will be appreciated that, although specific embodiments of the invention have been described herein for purposes of illustration, various modifications may be made without deviating from the spirit and scope of the invention. The invention, thus, is not limited except as by the appended claims hereto.

We claim:

1. A pump assembly coupleable to a source of liquefied gas, the pump assembly comprising:
   a pump module having a pump driver;
   a cooling assembly positioned generally adjacent to the pump module, the
   cooling assembly having a converging pump head receiving aperture, the cooling assembly having a fluid inlet line and a fluid outlet line in fluid communication with the source of liquefied gas and in fluid communication with the pump head receiving aperture; and
   a pump head assembly removably retained in the pump head receiving aperture, a portion of the cooling assembly being intermediate the pump head assembly and the pump module, the pump head assembly having a converging shape and being sized to engage the cooling assembly in a wedged configuration when the pump assembly is in an installed position in the cooling assembly, the pump head having a fluid inlet pathway abutting in direct sealable engagement with the fluid inlet line of the cooling assembly, and having a fluid outlet pathway abutting in direct sealable engagement with the fluid outlet line of the cooling assembly, the pump head assembly being operably coupled to the pump driver of the pump module to provide a flow of the liquefied gas from the fluid inlet line, through the pump head assembly, and to the outlet line.

2. The pump assembly of claim 1 wherein the pump head assembly is removable from the cooling assembly while the cooling assembly remains adjacent to the pump module.

3. The pump assembly of claim 1 wherein the pump head assembly is removable from the cooling assembly by extracting the pump head assembly generally axially away from the pump head receiving aperture, thereby automatically terminating the abutting interconnection of the fluid inlet pathway and the fluid inlet line, and the abutting interconnection of the fluid outlet pathway and the fluid outlet line.

4. The pump assembly of claim 1, further comprising an inlet check valve assembly in fluid communication with the fluid inlet line and an outlet check valve assembly in fluid communication with the fluid outlet line, at least one of the inlet and outlet check valve assemblies being wedged into sealable engagement between the cooling assembly and the pump head assembly, the inlet and outlet check valve assemblies positioned to allow the liquefied gas to be pumped through the pump head assembly in only one direction.

5. The pump assembly of claim 1 wherein the pump head assembly has an inlet check valve in fluid communication with the fluid inlet line and an outlet check valve in fluid communication with the fluid outlet line, the inlet and outlet check valves being positioned to allow the liquefied gas to be pumped through the pump head assembly in only one direction.

6. The pump assembly of claim 1, further comprising an inlet check valve in fluid communication with the fluid inlet line, the inlet check valve being positioned to allow the liquefied gas to be pumped through the pump head assembly in only one direction.

7. The pump assembly of claim 1, further comprising an outlet check valve in fluid communication with the fluid outlet line, the outlet check valve being positioned to allow the liquefied gas to be pumped through the pump head assembly in only one direction.

8. The pump assembly of claim 1 wherein the pump head assembly has a plunger receptacle therein in fluid communication with the fluid inlet and outlet pathways, and the pump driver includes a plunger reciprocally received in the plunger receptacle and axially moveable along an aspirating stroke and a discharge stroke.

9. The pump assembly of claim 8 wherein the pump head assembly has a primary portion made of a first material and an insert in the primary portion formed of a second material different from the first material, the insert being in fluid communication with the fluid inlet and outlet pathways, and the primary portion is out of direct fluid communication with the fluid inlet and outlet pathways so the liquefied gas is isolated from and out of direct engagement with the first material.

10. The pump assembly of claim 1 wherein the cooling assembly includes a body portion and first and second fluid line fittings connected to the body portion, the first fluid line fitting has the fluid inlet line extending therethrough, and the second fluid line fitting has the fluid outlet line extending therethrough, the first and second fluid line fittings are configured so the liquefied gas is isolated from and out of direct engagement with the body portion.

11. The pump assembly of claim 10 wherein the body portion is made of a first material and at least one of the first and second fluid line fittings is made of a second material different from the first material.

12. The pump assembly of claim 1, further including a lock mechanism connected to the pump head assembly and configured to releasably retain the pump head assembly in the installed position in the cooling assembly.

13. The pump assembly of claim 1 wherein the pump head assembly includes at least one of an inlet check valve in fluid communication with the fluid inlet line and an outlet check valve in fluid communication with the fluid outlet line, the at least one of the inlet and outlet check valves being positioned to allow the liquefied gas to be pumped through the pump head body in only one direction.

14. The pump assembly of claim 1 wherein the pump head assembly has a pump head body and an insert therein positioned at least partially in the pump head body, and further comprising an inlet check valve connected to the pump head body in fluid communication with the fluid inlet line and an outlet check valve connected to the pump head body and in direct fluid communication with the fluid outlet line, the inlet and outlet check valves being positioned to allow the liquefied gas to be pumped through the pump head body in only one direction, the insert has a plunger receptacle therein in direct fluid communication with the fluid inlet and outlet pathways, the pump head body and insert are configured so the liquefied gas is isolated from and out of direct engagement with the pump body.

15. The pump assembly of claim 14 wherein the cooling assembly includes a body portion made of a first material, a first fluid line fitting through which the fluid inlet line extends, and a second fluid line fitting through which the fluid outlet line extends, the first and second fluid line fittings are made of a second material different from the first material so the liquefied gas is isolated from and out of direct engagement with the body portion of the cooling assembly.

16. The pump assembly of claim 1 wherein the body portion of the cooling assembly is made of aluminum.

17. The pump assembly of claim 1, further comprising a chiller assembly connected to the pump head assembly to chill the pump head assembly to a selected temperature.

18. The pump assembly of claim 17 wherein the chiller assembly is a thermoelectric chiller assembly.

19. The pump assembly of claim 17 wherein the cooling assembly includes a plurality of pathways therethrough, and the chiller assembly is a re-circulating cooling bath that directs a flow of chilled cooling fluid through the plurality of pathways to chill the cooling assembly, thereby chilling the pump head assembly.

20. The pump assembly of claim 1, further comprising a chiller assembly having a chilling pathway therethrough in fluid communication with the liquefied gas before the liquefied gas enters the fluid inlet line, the chiller assembly being configured to chill the liquefied gas as the liquefied gas flows through the chilling pathway before the liquefied gas is pumped through the pump head assembly.

21. The pump assembly of claim 1 wherein the pump head assembly is slidably removable from the cooling assembly and the pump module, wherein the fluid inlet and outlet lines in the cooling assembly are slidably removed from fluid interconnection with the fluid inlet and outlet pathways, respectively, upon removing the pump head assembly from the pump head receiving aperture in the cooling assembly.

22. The pump assembly of claim 1 wherein the pump head assembly is removable from the cooling assembly and the pump module without mechanically disconnecting the fluid inlet and outlet lines from the fluid inlet and outlet pathways, respectively.

23. The pump assembly of claim 1 wherein the fluid inlet and outlet lines in the cooling assembly are in abutting engagement with the fluid inlet and outlet pathways, respectively, in the pump head free of direct mechanical interconnection therebetween.

24. The pump assembly of claim 1, further comprising a piston assembly reciprocally connected to the pump head assembly and being movable along an aspiration stroke and a discharge stroke, the discharge stroke includes a fluid compression portion and a fluid discharge portion, the fluid compression portion is approximately 30 percent of the full discharge stroke and the fluid delivery portion is approximately 70 percent of the full discharge stroke, and the pump driver in the pump module is coupled to the piston assembly, the pump driver having a drive shaft that engages the piston assembly to cause reciprocal movement of a plunger in the plunger assembly along the aspiration and discharge strokes, the pump driver includes a cam coupled to the drive shaft, the cam being shaped to provide the full aspiration stroke of the piston assembly upon rotation of the cam through approximately 130°–150°, to cause the compression portion of the discharge stroke upon rotation of the cam through approximately 30°–50°, and to cause the fluid delivery portion of the discharge stroke upon rotation of the cam through approximately 170°–190°.

25. The pump assembly of claim 1, further comprising a pump mechanism coupled to and activated by the pump driver, the pump mechanism being configured to be in fluid communication with a source of at least one of a lubricating fluid and a solvating fluid, the pump mechanism being activatable to introduce one of the lubricating fluids and solvating fluids into the flow of liquified gas before the flow of liquified gas reaches the pump head assembly.

26. A pump assembly coupleable to a source of liquefied gas, the pump assembly comprising:

a pump module;

a cooling assembly positioned generally adjacent to the pump module, the cooling assembly having a pump head receiving aperture;

a pump head assembly removably retained in the pump head receiving aperture, a portion of the cooling assembly being intermediate the pump head assembly and the pump module, the pump head assembly being operably coupled to the pump driver of the pump module to provide a flow of the liquefied gas through the pump head assembly;

a piston assembly reciprocally connected to the pump head assembly and being movable along an aspiration stroke and a discharge stroke, the discharge stroke includes a fluid compression portion and a fluid discharge portion, the fluid compression portion is approximately 30 percent of the full discharge stroke and the fluid delivery portion is approximately 70 percent of the full discharge stroke; and a pump driver connected to the pump module and coupled to the piston assembly, the pump driver having a drive shaft that engages the piston assembly to cause reciprocal movement of the piston assembly along the aspiration and discharge strokes, the pump driver includes a cam coupled to the drive shaft, the cam being shaped to provide for the full aspiration stroke of the piston assembly upon rotation of the cam through approximately 130°–150°, to cause the compression portion of the discharge stroke upon rotation of the cam through approximately 30°–50°, and to cause the fluid delivery portion of the discharge stroke upon rotation of the cam through approximately 170°–190°.

27. The pump assembly of claim 26 wherein the cam is shaped to provide for the aspiration stroke upon rotation of the cam through approximately 140°, the compression portion of the discharge stroke upon rotation of the cam through approximately 40°, and the fluid delivery portion of the discharge stroke upon rotation of the cam through approximately 180°.

28. A pump assembly coupleable to a source of liquefied gas, the pump assembly comprising:

a pump module having a pump driver;

a cooling assembly adjacent to the pump module and having a pump head receiving aperture defined by a pair of spaced apart first and second side wall portions that extend from a front surface toward the pump module and that converge toward each other, the cooling assembly having a fluid inlet line extending through the first side wall portion, and having a fluid outlet line extending through the second side wall portion, the fluid inlet and outlet lines being in fluid communication with the source of liquid gas and with the pump head receiving aperture; and a pump head assembly removably retained in the pump head receiving aperture with a portion of the cooling assembly being intermediate the pump head assembly and the pump module, the pump head body having a converging shape and being shaped and sized to be positioned between the converging first and second side wall portions of the cooling assembly and to frictionally engage the first and second side wall portions in a wedged configuration when in an installed position, the pump head assembly being removable from the cooling assembly while the cooling assembly remains adjacent to the pump module, the pump head body having a first side portion with a fluid inlet pathway therethrough and positioned to abut in direct sealable engagement with the fluid inlet line of the first side wall portion of the cooling assembly, and having a second side portion with a fluid outlet pathway therethrough and positioned to abut in direct sealable engagement with the fluid outlet line of the second side wall portion of the cooling assembly, the pump head assembly reciprocally receiving a portion of the piston assembly in a piston receptacle and configured to provide a flow of the liquefied gas from the fluid inlet line, through the pump head assembly, and to the outlet line.

29. The pump assembly of claim 28, further comprising an inlet check valve and an outlet check valve, the inlet check valve being connected to the pump head body and being in fluid communication with the fluid inlet line, the outlet check valve being connected to the pump head body and in fluid communication with the fluid outlet line, the inlet and outlet check valves being positioned to allow the liquefied gas to be pumped through the pump head body in only one direction.

30. The pump assembly of claim 28 wherein the piston receptacle is in fluid communication with the fluid inlet and outlet pathways, and the piston assembly includes a piston reciprocally received in the piston receptacle for movement therein along an aspirating stroke and a discharge stroke.

31. The pump assembly of claim 30 wherein the pump head body has a primary portion made of a first material and further including an insert in the primary portion formed of a second material different from the first material, the insert being in fluid communication with the fluid inlet and outlet pathways so the liquefied gas is isolated from and out of direct engagement with the first material.

32. The pump assembly of claim 28 wherein the cooling assembly includes a body portion made of a first material, a first fluid line fitting through which the fluid inlet line extends, and a second fluid line fitting through which the fluid outlet line extends, the first and second fluid line fittings are made of a second material different from the first material and configured so the liquefied gas is isolated from and out of direct engagement with the first material.

33. The pump assembly of claim 28, further including a lock mechanism connected to the pump head assembly and configured to releasably retain the pump head assembly in an installed position in the cooling assembly.

34. The pump assembly of claim 28, further comprising a chiller assembly connected to the pump head assembly to chill liquefied gas to a selected temperature before the liquefied gas reaches the pump head assembly.

35. The pump assembly of claim 28 wherein the cooling assembly includes a plurality of pathways therethrough, and further comprising a recirculating cooling bath that directs a flow of chilled cooling fluid through the plurality of pathways to chill the cooling assembly, thereby chilling the pump head assembly.

36. The pump assembly of claim 28 wherein the pump head assembly is removable from the cooling assembly and the pump module without mechanically disconnecting the fluid inlet and outlet lines from the fluid inlet and outlet pathways, respectively.

37. The pump assembly of claim 28 wherein the fluid inlet and outlet lines in the cooling assembly are in abutting engagement with the fluid inlet and outlet pathways, respectively, free of direct mechanical interconnection therebetween.

38. A pump head assembly and cooling assembly for use with a pump module to pump liquid gas, comprising:

a cooling assembly having a pump head receiving aperture defined by converging first and second side wall portions, the cooling assembly having a fluid inlet line extending through the first side wall portion and having a fluid outlet line extending through the second side wall portion, the fluid inlet and outlet lines being configured to carry the liquid gas therethrough; and a pump head assembly removably retained in the pump head receiving aperture with a portion of the cooling assembly configured to be intermediate the pump head assembly and the pump module, the pump head assembly having a pump head body with a partial wedge-shape and being sized to be wedged into frictionally engagement with the cooling assembly when in an installed position, the pump head body having a first side portion with a fluid inlet pathway positioned to sealably abut the fluid inlet line of the first side wall portion of the cooling assembly when the pump head assembly is in the installed position, and having a second side portion with a fluid outlet pathway positioned to abut the fluid outlet line of the first side wall portion of the cooling assembly when the pump head assembly is in the installed position.

* * * * *